(12) United States Patent
Cosman et al.

(10) Patent No.: US 7,862,563 B1
(45) Date of Patent: Jan. 4, 2011

(54) INTEGRAL HIGH FREQUENCY ELECTRODE

(76) Inventors: Eric R. Cosman, 872 Concord Ave., Belmont, MA (US) 02478-0002; Eric R. Cosman, Jr., 872 Concord Ave., Belmont, MA (US) 02478-0002

( * ) Notice: Subject to any disclaimer, the term of this patent is extended or adjusted under 35 U.S.C. 154(b) by 1182 days.

(21) Appl. No.: 11/488,153

(22) Filed: Jul. 18, 2006

Related U.S. Application Data

(63) Continuation-in-part of application No. 11/355,960, filed on Feb. 17, 2006, now abandoned.

(60) Provisional application No. 60/654,293, filed on Feb. 18, 2005.

(51) Int. Cl.
A61B 18/14 (2006.01)

(52) U.S. Cl. .......................... 606/41; 606/49
(58) Field of Classification Search .................... 606/41, 606/48–50
See application file for complete search history.

(56) References Cited

U.S. PATENT DOCUMENTS

| | | | | |
|---|---|---|---|---|
| 3,825,004 A | * | 7/1974 | Durden, III | 604/20 |
| 4,483,338 A | | 11/1984 | Bloom et al. | |
| 4,565,200 A | | 1/1986 | Cosman | |
| 4,682,596 A | | 7/1987 | Bales et al. | |
| 4,907,589 A | * | 3/1990 | Cosman | 606/34 |
| 4,936,281 A | | 6/1990 | Stasz | |
| 4,966,597 A | * | 10/1990 | Cosman | 606/50 |
| 4,998,933 A | | 3/1991 | Eggers et al. | |
| 5,178,620 A | | 1/1993 | Eggers et al. | |
| 5,336,176 A | | 8/1994 | Yoon | |
| 5,348,554 A | * | 9/1994 | Imran et al. | 606/41 |
| 5,454,809 A | | 10/1995 | Janssen | |
| 5,486,161 A | | 1/1996 | Lax et al. | |
| 5,500,012 A | | 3/1996 | Brucker et al. | |
| 5,520,684 A | | 5/1996 | Imran | |
| 5,545,161 A | | 8/1996 | Imran | |
| 5,554,110 A | | 9/1996 | Edwards et al. | |
| 5,599,346 A | * | 2/1997 | Edwards et al. | 606/41 |
| 5,658,278 A | | 8/1997 | Imran et al. | |
| 5,688,267 A | | 11/1997 | Panescu et al. | |
| 5,782,760 A | | 7/1998 | Schaer | |
| 5,951,546 A | * | 9/1999 | Lorentzen | 606/41 |
| 6,146,380 A | | 11/2000 | Racz et al. | |
| 6,241,702 B1 | | 6/2001 | Lundquist et al. | |
| 6,325,800 B1 | * | 12/2001 | Durgin et al. | 606/45 |
| 6,440,127 B2 | | 8/2002 | McGovern et al. | |

(Continued)

FOREIGN PATENT DOCUMENTS

WO    WO 96/18349    6/1996

(Continued)

OTHER PUBLICATIONS

Cosman, et al., "Theoretical Aspects of Radiofrequency Lesions in the Dorsal Root Entry Zone", Neurosurgery, vol. 15, No. 6, pp. 945-950, (1984).

(Continued)

*Primary Examiner*—Michael Peffley
(74) *Attorney, Agent, or Firm*—Steptoe & Johnson LLP

(57) ABSTRACT

A method and apparatus for the application of an electrical signal to neural tissue and other target tissue in the living body.

79 Claims, 18 Drawing Sheets

U.S. PATENT DOCUMENTS

| | | |
|---|---|---|
| 6,447,505 B2 | 9/2002 | McGovern et al. |
| 6,478,793 B1 * | 11/2002 | Cosman et al. ............... 606/34 |
| 6,506,189 B1 | 1/2003 | Rittman et al. |
| 6,517,534 B1 | 2/2003 | McGovern et al. |
| 6,530,922 B2 | 3/2003 | Cosman et al. |
| 6,602,248 B1 * | 8/2003 | Sharps et al. ................ 606/32 |
| 6,669,652 B2 | 12/2003 | Anderson et al. |
| 6,692,493 B2 | 2/2004 | McGovern et al. |
| 6,743,226 B2 | 6/2004 | Cosman et al. |
| 6,827,715 B2 | 12/2004 | Franischelli et al. |
| 7,077,842 B1 | 7/2006 | Cosman |
| 7,104,987 B2 | 9/2006 | Biggs et al. |
| 7,306,596 B2 | 12/2007 | Hillier et al. |
| 7,318,822 B2 | 1/2008 | Darmos et al. |
| 7,377,918 B2 | 5/2008 | Amoah |
| 7,387,626 B2 | 6/2008 | Edwards et al. |
| 2005/0267459 A1 | 12/2005 | Belhe et al. |
| 2005/0267552 A1 | 12/2005 | Conquergood et al. |

FOREIGN PATENT DOCUMENTS

| | | |
|---|---|---|
| WO | WO 96/34571 | 11/1996 |
| WO | WO99/40859 | 8/1999 |
| WO | WO99/40860 | 8/1999 |
| WO | WO00/59394 | 12/2000 |

OTHER PUBLICATIONS

Gervais, et al., "Radio-frequency Ablation of Renal Cell Carcinoma: Early Clinical Experience[1]", Radiology, vol. 217, No. 3, pp. 665-672, (2000).

Goldberg, et al., "Tissue Ablation with Radiofrequency: Effect of Probe Size, Gauge, Duration, and Temperature on Lesion Volume", Acad. Radiol., vol. 2, No. 5, pp. 399-404, (1995).

Goldberg, et al., "Thermal Ablation Therapy for Focal Malignancy; a Unified Approach to Underlying Principles, Techniques, and Diagnostic Imaging Guidance", AJR, vol. 174, pp. 323-331, (2000).

* cited by examiner

| 400 | INSERT A ONE-PIECE ELECTRODE SO THAT THE UNINSULATED TIP OF THE ELECTRODE IS POSITIONED TO TREAT A NERVE OF THE SPINE, THE ELECTRODE HAVING A SHAFT COMPRISING A TUBING AND HAVING A SHARPENED DISTAL TIP THAT IS FORMED FROM AT LEAST A PORTION OF THE TUBING, THE ELECTRODE BEING ADAPTED FOR SELF-SUPPORTING, TISSUE-PIERCING PENETRATION THROUGH THE SKIN AND THE TISSUE OF A PATIENT'S BODY TO APPROACH A NERVE OF THE SPINE, AND THE ELECTRODE HAVING A TEMPERATURE SENSOR AT THE UNINSULATED TIP, AND HAVING A TEMPERATURE SENSOR CONNECTION AND A HIGH FREQUENCY CONNECTION AT THE PROXIMAL END OF THE ELECTRODE. |

↓

| 404 | CONNECT THE HIGH FREQUENCY CONNECTION AND THE TEMPERATURE SENSOR CONNECTION TO A HIGH FREQUENCY GENERATOR. |

↓

| 407 | DELIVER A SIGNAL OUTPUT FROM THE HIGH FREQUENCY GENERATOR TO THE NERVE OF THE SPINE THROUGH THE UNINSULATED TIP, WHILE MEASURING THE TEMPERATURE AT THE TEMPERATURE SENSOR, TO TREAT PAIN RELATED TO THE NERVE OF THE SPINE. |

FIG. 11

INTEGRAL HIGH FREQUENCY ELECTRODE

CLAIM OF PRIORITY

This application is a continuation-in-part of U.S. application Ser. No. 11/355,960, filed on Feb. 17, 2006, (now abandoned) which claims priority under 35 U.S.C. 119(e) to U.S. Provisional Application No. 60/654,293, filed on Feb. 18, 2005, each of which is incorporated by reference in its entirety.

TECHNICAL FIELD

This invention relates generally to field therapy.

BACKGROUND

The use of radiofrequency (RF) generators and electrodes to be applied to tissue for pain relief or functional modification is well known. For example, the RFG-3C RF lesion generator of Radionics, Inc., Burlington, Mass. and its associated electrodes enable electrode placement of the electrode near target tissue and heating of the target tissue by RF power dissipation of the RF signal output in the target tissue. Temperature monitoring of the target tissue by a temperature sensor in the electrode can control the process. Heat lesions with target tissue temperatures of 60 to 95 degrees Celsius are common. Tissue dies by heating above about 45 degrees Celsius, so this process produces the RF heat lesion.

RF generators and electrodes are used to treat pain and other diseases. Examples are the equipment and applications of Radionics, Inc., Burlington, Mass. such as the RFG-3C RF lesion generator and the SMK electrode and other electrode systems. Related information is given in the paper by Cosman ER and Cosman BJ, "Methods of Making Nervous System Lesions", in Wilkins RH, Rengachary S (eds.); Neurosurgery, New York, McGraw Hill, Vol. 3, 2490-2498; and is hereby incorporated by reference in its entirety.

The Radionics Pole Needle and RF Pole Needle have a shaft including a metal tubing with sharp distal end for insertion into tissue to reach a spinal target. The shaft of the RF pole needle is insulated except for an exposed conductive tip portion and has an electrical connection to a signal generator for delivery of stimulation or RF signal outputs to the target tissue. Each has a flexible injection tube and a port to allow injection of contrast, anesthetic, or saline solution fluid to the target tissue. Neither incorporates a built-in temperature sensor or adaptation to accept a temperature sensor. This has a disadvantage in RF lesion making because temperature monitoring of target tissue can be of significance to control the lesion process. Related information is given in Radionics brochures "Disposable RF cannula and RF electrodes, Pole Needles, and Injection Needles", brochure number 700xxx, SMK-C/Pole N.-5/74-0, copyright 2987, Radionics, Inc., and is herby incorporated by reference herein in its entirety.

The Radionics SMK Kit includes an insulated cannula having a pointed metal shaft that is insulated except for an uninsulated electrode tip. The cannula has a hub at its proximal end having a luer fitting to accommodate a separate thermocouple (TC) electrode that can deliver electrical signal output such as RF voltage or stimulation to the uninsulated electrode tip. A disadvantage of this system is that fluid injection into the cannula cannot be achieved when the TC electrode is also in the cannula. Another disadvantage is that the temperature sensor probe and the cannula are separate elements, which increases the complexity of the components needed for the system. Related information is given in the Radionics brochure "Type SMK Sluijter-Mehta Kit", number 700-1049-6-1991, copyright 1991, Radionics, Inc., and is hereby incorporated by reference in its entirety.

The Neurotherm Disposable Stimject kit includes a cannula that is insulated except for an exposed conductive tip. The cannula has a hub with a luer fitting. The Stimject kit has a "Tconnector" which is separate from the cannula and is connected to the luer fitting of the cannula after the cannula is inserted into the living body of the patient. The Tconnector has a flexible side port including flexible tubing that enters the side of the Tconnector. The tubing has on its end, a luer fitting that can accept a TC electrode. The TC electrode is separate from the Tconnector and the cannula, and comes as part of the Stimject kit. Once the cannula, Tconnector, and TC electrode are locked together, then injection, stimulation, and RF signal output can be applied without further connection to the cannula. One disadvantage is that the cannula, the injection port element (the Tconnector), and the TC electrode are all separate elements that must be connected together during the procedure and after the cannula is placed in the patient. This increases complexity, manipulations, and time of the procedure. Manipulations can cause movement of the cannula once it is properly placed at the target tissue, which has the disadvantage of losing accuracy of the procedure. Related information is given in the RDG Medical brochure "NeuroTherm Disposable Stimject Kit", brochure number RF104, 2004; and is hereby incorporated by reference herein in its entirety.

The LCE-TC, KCTE-TC, and TCE-TC electrodes of Radionics, Inc. are designed for making RF heat lesions in the spinal cord. They have very small diameter metal tubing shafts and uninsulated electrode tips, which is required for cordotomy application since the target tissue inside the spinal cord is very small and critical. The LCE-TC and KTCE-TC electrodes have shaft diameters of approximately 0.3 mm corresponding to 0.013" and 29 gauge stainless steel tubing shafts. A pointed tip at the distal end of the uninsulated electrode tip is in the shape of a conical point formed by welding shut the metal tubing of the shaft. The TCE-TC electrodes have shaft diameter of 0.5 mm, corresponding to 0.020" and 25 gauge stainless steel tubing shaft. A pointed tip at the distal end of the uninsulated electrode tip is in the shape of a conical point formed by welding shut the metal tubing of the shaft. Built into the tip of these electrodes is a thermocouple temperature sensor. The Radionics prospectuses on these electrodes are hereby incorporated by reference in its entirety. The LCE-TC and KTCE-TC electrodes have an integrally connected, non-separable, flexible electrical connection at its hub (or proximal) shaft end that enables connection to a RF generator. The TCE-TC electrode has a connection for the high frequency and the temperature sensor connection is inseparably built into its hub. The electrodes are very thin and flexible and are used to for RF heat lesion making in tiny target tissues in the spinal cord. One disadvantage is that these electrodes require an ancillary guidance needle or cannula to enable initial penetration of the skin and guidance through tissues of the neck. These electrodes have another disadvantage in that they require a separate depth stop to verniate their depth of penetration. Another disadvantage that these electrodes require multiple, separate parts to be used, which increases the complexity of the equipment and the cost to build it. Another disadvantage is that the metal tubing shafts with diameters of 0.3 to 0.5 mm are too flexible and delicate for self-supported penetration of skin and tissue on the way towards a nerve target near the spinal cord or spinal nerves. A further disadvantage is that the uninsulated electrode tip diameters of about 0.3 to 0.5 millimeters are also too small to make adequate-sized heat lesions in the spinal nerves and ganglia in many clinical situations. The electrodes also have another disadvantage in that their conical shaped pointed tips are not optimal for penetration of tough tissue on the way into the region the spinal facet joints and dorsal root ganglion. The electrodes also have no capability of injecting fluid directly through them, which is useful in some clinical situations.

The Cool-Tip Electrode of Radionics and Valley Lab, Inc. is a 16-gauge (or 1.6 millimeter diameter) electrode with partially insulated shaft and water-cooling channel inside its rigid cannula shaft. The brochure from Radionics is hereby incorporated by reference in its entirety. The Cool-Tip Electrode is used specifically for making very large RF heat ablations of cancerous tumors, primarily in soft-tissue organs. It has a closed trocar point that includes a metal plug that is welded to the metal tubing that is part of the electrode shaft. The distal end of the metal plug is sharpened to form a three sided, axially symmetric trocar. The distal end is a closed and sealed metal structure. The sharpened portion of the distal tip does not include the metal tubing itself, but rather the sharpened end of the metal plug that is welded to the metal tubing. This has a disadvantage in that it is a more complex construction involving multiple substructures and multiple construction operations such as welding the trocar point to the metal shaft. The temperature sensor is built into the electrode distal tip, and it is configured to measure the temperature of cooling fluid in the inner space of the metal tubing of the electrode shaft. This has a disadvantage that the temperature sensor has reduced speed and accuracy in measuring tissue temperature immediately outside the uninsulated electrode tip. Another disadvantage is that the temperature sensor can not be visualized from the outside because of the closed metal tip which makes it more difficult to determine its location inside the uninsulated electrode tip. The electrode has flexible RF electrical connection and flexible thermocouple wire connections that are connected to the proximal hub of the electrode shaft. The electrode has no adaptation for fluid injections through its shaft and into the target tissue. The 16-gauge cannula has too large a diameter for general use for RF applications on spinal nerves and ganglia, especially in the cervical region or near dorsal root ganglia. The thermocouple sensor in the Cool-Tip electrode is also located in the cooling fluid channel inside the distal end, and is not in close mechanical and thermal contact with the outer metal tubing of the uninsulated electrode tip, exposed electrode tip or to the surface of the exposed electrode tip. This has the disadvantage in that temperature measurement of tissue temperatures near the tip can be slow responding and inaccurate. Such a disadvantage can be inadequate for RF applications at spinal nerves or ganglia.

The RRE Electrode of Radionics, Inc. has a 16 gauge metal tubing shaft that is insulated except for an uninsulated electrode tip that has a trocar distal point. It has a shaft and an integrally attached hub. The Radionics prospectus on the RRE electrode is hereby incorporated by reference in its entirety. The RRE electrode shaft includes a 16 gauge metal tubing. Its symmetrical three-sided trocar tip is formed by welding onto the metal tubing a stainless steel plug that is than ground to have a trocar pointed tip end. It has a unitized construction with closed metal tip. This has one disadvantage in that the position of the temperature sensor inside the electrode cannot be visualized checked from the outside during or after assembly. The RRE electrode has a closed trocar point that includes a metal plug that is welded to the metal tubing that is part of the electrode shaft. The distal end of the metal plug is sharpened to form a three sided, axially symmetric trocar. The distal end is a closed and sealed metal structure. The sharpened portion of the distal tip does not include the metal tubing itself, but rather the sharpened end of the metal plug that is welded to the metal tubing. This has a disadvantage in that it is a complex construction involving multiple substructures and multiple construction operations such as welding the trocar point to the metal shaft. The tip and shaft are in a straight-line geometry. This has one disadvantage, compared to a curved-tip electrode, in that the electrode cannot be steered as easily as a curved-tip shaft, and its tip can not be contoured or curved next to a curved nerve path as is often convenient for the facet nerve treatments. The RRE electrode has a temperature sensor inside the metal tubing at the distal tip and near the welded on stainless steel plug that is part of the trocar point. The temperature sensor is not at the external surface of the electrode distal tip. This has one disadvantage in that the temperature readings are not made immediately in contact with the target tissue that is being treated during a high frequency therapy, which can degrade the effectiveness of the procedure. Another disadvantage is that because the temperature sensor is not close to the very tip and surface of the uninsulated electrode tip, the temperature measurements can be slow and inaccurate. Another disadvantage is that the position of the temperature sensor with respect to the metal tubing and the metal trocar plug cannot be seen externally, and thus cannot be visually inspected from the outside. This has the disadvantage that the temperature sensor may not be in close thermal contact with the tubing wall or the trocar tip, which reduces the speed of response and the accuracy of the temperature readings. Another disadvantage is that the position of the temperature sensor, which is important for the accuracy of temperature measurement, cannot be easily checked during or after electrode assembly. Because of the thickness of the metal tubing and the trocar tip, the electrode tip structure has a significant thermal mass, and the temperature sensor is not in close thermal contact with the outer wall of the tubing. This has a disadvantage that its thermal response to temperature changes in the tissue immediately outside the RF tip is slow. Another disadvantage is that the RRE electrode construction is complex, expensive, and does not lend itself to full inspection of it internal structure. The RRE electrode does not have flexible electrical connections for the high frequency signal or the temperature sensor signal. This has a disadvantage that, once the electrode is placed at the target in the patient body, any connection of wires to the high frequency generator can disturb the proper electrode position, causing inaccuracies in the clinical procedure. The RRE electrode does not have a radio opaque material of significantly different radio opacity form the stainless steel of the tubing and the trocar point. This has a disadvantage that a clear discrimination of the position of the electrode tip under x-ray control can be made difficult or unclear.

The TCE-TC and the stereotactic electrodes of Radionics, Inc. have unitized construction of a metal tubing shaft, a hub with non-flexible electrical connections for temperature sensing and high frequency generator signal outputs, and closed metal construction of their uninsulated electrode tip. The Radionics prospectuses are hereby incorporated by reference in their entirety. The stereotactic electrodes have typically rounded tip ends. This has one disadvantage that they are not appropriate for self-penetration of skin and tissue around the spine. The TCE-TC electrode has a 0.5 mm shaft diameter and a conically pointed distal tip. It is designed to be carried inside a guide needle of 1.3 mm outer diameter. The guide needle is used to first penetrate the skin and tissue of the neck before the TCE-TC electrode is inserted through the guide needle. The point of the TCE electrode is used only to pierce and penetrate the spinal cord in the final step of a cordotomy pain procedure. The TCE electrode by itself is too thin and flexible to be used to self-penetrate skin, musculature, and other connective tissue of the spinal region, which is involved in performing percutaneous facet denervations and dorsal root ganglion procedures.

SUMMARY

The present invention relates to a system and method involving an integral high frequency electrode system that has a shaft that is rigid enough for self-supported penetration of skin and tissue near the spine, the shaft being insulated over a portion of its surface and having an uninsulated electrode tip with a sharpened distal tip point, and a built-in temperature sensor at the uninsulated electrode tip configured to be in close thermal contact with the electrode tip to enable fast and accurate temperature monitoring of target tissue near the tip during high frequency application.

In one example, the integral high frequency electrode system can include a unitized electrode system, also described or referred to as a one-piece electrode system, or an integrated electrode system, in which the parts of the electrode system are constructed to be inseparable, or built into a single unit. The integral electrode system can include a unitized combination of non-separable components, which can be described as a unitized electrode system. In one example, a needle can include a metal tubing shaft that is insulated over at least a portion of its surface and has an uninsulated electrode tip at its distal end. The distal end can have a pointed distal tip end that includes at least in part, a beveled portion of the metal tubing shaft. A temperature sensor can be built into the distal tip and positioned in close thermal contact with the wall of the metal tubing at the uninsulated electrode tip to enable fast and accurate temperature measure of the target tissue near the tip during high frequency treatment of the tissue. There can be a high frequency connection at the proximal end of the needle shaft that can connect to a high frequency generator to provide signal outputs from the high frequency generator to be applied to the target tissue through the uninsulated electrode tip. There can be a temperature sensor connection at the proximal end of the needle shaft that connects to a temperature read-out apparatus and connects to the temperature sensor, so that fast and accurate temperature measurements of the target tissue can be obtained during high frequency applications.

In another example, a method of treating spinal nerves can include a percutaneous insertion of the self-supported needle electrode through the skin and tissue near the spine to place the uninsulated electrode tip at target tissue near a spinal nerve or a dorsal root ganglion. The electrode can include a metal tubing in its shaft that is sufficiently large in diameter and sufficiently rigid that it can withstand a forceful manual manipulation so that the electrode tip can be navigated by hand to a desired critical target position near the spinal nerve. A high frequency generator can be connected to the electrode by the high frequency connection and by the temperature connection, and signal outputs from the generator can be applied to the target tissue while monitoring the temperature of the target tissue. In one example, the high frequency signal output application can cause heating of the target tissue and the spinal nerve, which can be used to reduce spinal pain.

In another example, a needle element can have a rigid tubular shaft and a built-in TC element in its distal tip at the uninsulated RF electrode tip. Wires inside the needle can connect to the TC element and can be inseparably connected at the proximal end to a flexible connection portion that can connect to an external temperature monitor. An RF electrical connection can enable the connection of an RF signal to the uninsulated electrode distal tip. It can include a flexible wire element that is inseparably attached to the proximal end of the needle. This enables connection to an external RF signal source. This integral and non-separable RF electrode system can include a metal shaft or cannula as part of the needle. For example, the cannula can include a metal tubing having diameter in the range of 0.56 mm or larger which corresponds to 24 gauge or larger. This can be a suitable cannula diameter range for use in RF applications to spinal nerves and ganglia. This diameter range can be suitable for self-supported skin and tissue penetration and target guidance, without the need for a secondary guide needle. One advantage is that the electrode can be inserted into the body percutaneously and by hand under x-ray control. Another advantage is that that it eliminates the need to remove a stylet or to insert a TC or RF element and the use of a separate guide cannula. Another advantage is that it reduces the number of separable components, which reduces complexity of manufacturing the complexity in the operation suite, and reduces costs. Another advantage is that it increases efficiency of the procedure and reduces the risk of movement of electrode positioning due to manipulation.

In another example, a system can include an integral high frequency needle electrode having a rigid shaft for self-supported percutaneous insertion through the skin and tissue near the spine, a temperature sensor in a uninsulated electrode tip at the distal end of the electrode, inseparable electrical connections for connection to a high frequency generator, and an inseparable temperature connection that connects to the temperature sensor and to a temperature readout apparatus. The system can further include a fluid port at its proximal end and a fluid channel through the electrode with a fluid opening near the distal tip of the electrode, so that fluid can be injected through the electrode system into target tissue near the distal tip. In one example, the fluid port can include a flexible fluid tubing that is inseparably attached to the proximal end of electrode shaft, so that fluid can be injected into the target tissue without undesired stress and pulling on the electrode shaft. One advantage is that fluid, such as saline, contrast agent, or anesthetic can be injected into the target tissue during the procedure without disconnecting components and without undesired disturbance of the electrode position near the target tissue. Another advantage is that there are fewer components to the electrode system, which reduces complexity and costs.

In one aspect, a method for treating spinal nerves can include using the integral high frequency electrode near a facet joint nerve, or a dorsal root ganglion, or an inter-vertebral disc. High frequency signal output can be applied from a high frequency generator to the target tissue through the uninsulated electrode tip while monitoring temperature of the target tissue by the temperature sensor. The target tissue can be heated by the high frequency signal output to relieve pain. Fluid can be injected into the target tissue before or during the high frequency application to suit clinical needs without need to remove or replace components. One advantage is that this simplifies the procedure and reduces the chance of disturbing the electrode position.

In one example, the integral high frequency electrode can have a curved shape of it distal tip. One advantage of this is that it allows steering of the electrode tip into the position of the target tissue. Another advantage is that the curved uninsulated electrode tip can be laid against a spinal nerve that curves along for example, the bone near the facet joint. Another advantage is that that a curved distal tip can be directed more obliquely toward a spinal nerve, which is desired in some clinical approaches.

In various examples, the distal tip point and the temperature sensor within it can be configured in a variety of geometries according to clinical needs or according to manufacturing efficiency and quality control. In one example, the point can be made by a bevel or multiple beveled surfaces of the metal tubing that is part of the shaft of the electrode. Another advantage is that this is a simple and inexpensive construction. Another advantage is that the temperature sensor can be positioned within the lumen of the bevel end of the metal tubing. One advantage of this is that the position of the temperature sensor can be visualized for quality control purposes. Another advantage is that the temperature sensor can be positioned so that it is in close thermal contact with the wall of the metal tubing tip. Another advantage is that the temperature sensor can be fused to the wall of the metal tubing at the distal tip under direct visual control. Another advantage is that the temperature sensor clinical needs be put in an improved thermal contact with the uninsulated electrode tip for improved temperature response.

In one example, a radio opaque material can be inserted into or onto the distal tip of the electrode. This enables better visualization to the electrode tip under x-ray control during the procedure. Another advantage is that this improves the positioning of the electrode tip at a desired target position.

In one example, an electrode system can include a needle element and an integrated combination of inject port, temperature sensor element, and high frequency connection element. In one example, the needle can include a rigid tubing that is insulated except for an exposed, uninsulated conductive tip. The needle can be integrally and inseparably connected to an injection port element. In one example, the inject port element can include a flexible tubing portion which is connected to the needle and is in fluid communication with the lumen inside the needle element. Fluid can be injected through the inject port into the lumen of the needle and emerges from the needle tip and into the target tissue near the distal end. The temperature sensor can be a TC that is integrally combined with a high frequency electrode to form a TC/high frequency element. The TC/high frequency element can be integrally and inseparably connected to the needle and the inject elements and enables monitoring of the temperature near the needle tip and enables connection to a high frequency generator to supply stimulation signals or high frequency signal output to the electrode uninsulated electrode tip. One advantage is that the integral structure of needle, injection port, and TC/high frequency element reduces the components and the steps the clinician must utilize to do a procedure. Another advantage is the increased accuracy and stability that is achieved by the unitized electrode system as compared to multi-component electrode systems that must be manipulated to exchange components during the procedure. The integral, inseparable combination of needle, injection element, and TC/high frequency element reduces the manipulation of the electrode system after it is positioned in the target tissue. In comparison to other existing electrode systems, such as for example the SMK electrode system, in which the cannula and TC/RF elements are separate and must be connected together during the procedure, the present system and method reduces the complexity of and the cost to make, sell, and use the equipment and steps to carry out the procedures, for example, in the spinal nerves.

In another example, the needle electrode can be integrated with a flexible inject port. The TC/RF element can be a separate element and can be inserted into the needle during the procedure. The needle, with flexible inject port integrally attached, can be inserted into the tissue of the living body. One advantage is that the integral needle element and flexible port element eliminates the need to connect these elements after the needle is in place at the target tissue site. This increases the efficiency, accuracy, and stability of the target positioning.

In another example, a first element can be a needle element that can be inserted into the tissue of the patient. A second element can be an integral and inseparable combination of an injection port element and a TC/RF element. Once the needle is inserted into the tissue, the second element can be inserted into and/or connected to the needle element to enable injection of fluid into the target tissue and to apply RF electrical signals through the needle to the target tissue while measuring temperature of the target tissue with the TC sensor. One advantage is that the combination eliminates the need to remove the injection element in order to use the TC/RF element after needle placement at the target tissue. Another advantage is that it reduces the risk of displacing the needle from the target position and reduces the manipulation of different elements during the procedure.

In one example, a TC element can be fused to the inner lumen of a needle element at its uninsulated electrode tip to provide an integral electrical union of the TC element with the needle while leaving the needle lumen adequately open to the passage of fluids that are injected through the inject port element and through the needle lumen.

Forms of the electrode system are disclosed herein in various embodiments. Specific embodiments with various examples of and forms of built in temperature sensor configurations, inject ports, tip geometries, and construction aspects are disclosed which are suited to clinical, manufacturing, efficiency, and economical needs.

In one aspect, a unitized high frequency electrode system can include a cannula having a proximal end and a distal end. The distal end can include an uninsulated electrode tip, and the cannula can be rigidly adapted to enable self-supported penetration of skin and tissue so that the uninsulated electrode tip can be positioned in a target tissue. The system can include a high frequency electrical connection that is inseparably connected to the proximal end and configured so that a high frequency signal connected to the high frequency electrical connection is connected to the uninsulated electrode tip, a temperature connection and a temperature sensor. The temperature sensor can be configured to be in thermal contact with the uninsulated electrode tip. The temperature connection can be connected to the temperature sensor and configured so that a temperature readout apparatus connected to the temperature connection can read the temperature at the temperature sensor. The high frequency electrode system, when inserted into the living body so that the uninsulated electrode tip is positioned in the tissue, enables the treatment of the tissue by applying the high frequency signal to the tissue while sensing the temperature of the tissue adjacent to the uninsulated electrode tip. The high frequency electrical connection can include a flexible high frequency portion. The temperature connection can include a flexible temperature portion that is inseparably connected to the proximal end. The tissue can be near a spinal nerve or spinal bones. The uninsulated electrode tip can include a metal tubing at its exterior surface. The temperature sensor can be in thermal contact with the metal tubing to enable rapid temperature measurement of the target tissue adjacent to the uninsulated electrode tip. The metal tubing can have a diameter of at least 0.4 millimeters. The cannula can include an inseparable injection port connected to the proximal end, and a fluid channel through the cannula and a fluid exit channel at the distal end, whereby fluid can be injected into the injection port and pass through the fluid channel and out of the cannula through the fluid exit channel. The inseparable injection port can further include a flexible fluid port connection.

The high frequency electrical connection and the temperature connection can include a flexible leader portion that is inseparably connected to the proximal end and a unitized hub connection at the proximal end that is adapted to connect to a high frequency generator. The flexible leader portion can include a single flexible tubing that is connected to the proximal end, the single flexible tubing having a tubing lumen within the single flexible tubing, the high frequency electrical connection includes at least one high frequency electrical wire passing within the tubing lumen, the temperature connection including at least one temperature wire passing within the tubing lumen, and the cannula further including a fluid channel through the cannula and a fluid exit channel near the distal end, the tubing lumen being fluid connected to the fluid channel in the cannula, and the flexible leader portion including an injection port, whereby fluid injected into the injection port passes through the tubing lumen, through the fluid channel, and out of the cannula through the fluid exit channel. The cannula can include a metal tubing, and the flexible leader portion includes a single flexible plastic tubing, the tubing lumen being a single lumen within the single flexible plastic tubing, the flexible leader portion having a proximal leader end and a distal leader end, the distal leader end being connected to the metal tubing, and the proximal leader end being connected to the hub connection and the injection port. The temperature connection can include a wire that runs in part through the interior space of the cannula and connects to the temperature sensor. The proximal end can be configured to be inaccessible to port-injection of fluid. The proximal end can be closed to injection of fluids into the interior space of the cannula. The proximal end can be sealed to the passage of fluids through the interior space of the cannula. The distal end of the cannula can include a curved portion to improve the positioning of the uninsulated electrode tip near the target tissue. The cannula can include a metal tubing. The uninsulated electrode tip can have a sharpened tip end. The sharpened tip end can include a tri-cut beveled point. The temperature sensor can include a constantan wire that passes through the interior space of the cannula and can be fused electrically to the wall of the metal tubing at the uninsulated electrode tip. The temperature sensor can include a copper and a constantan wire electrically fused to a thermocouple junction.

The unitized high frequency electrode system can further include a radio opaque material inside a lumen of the cannula near the uninsulated electrode tip to increase the contrast in an x-ray imaging of the electrode. The lumen at a beveled portion of the metal tubing at the distal end of the cannula can be occluded. The lumen can further be occluded by an epoxy. The distal end can have a sharpened distal tip that is not fully enclosed by metal. The sharpened distal tip can include a beveled portion of the metal tubing. The distal end of the metal tubing can include a tapered forming of the metal tubing that converges to a tissue piercing tip end. The cannula can be adapted so that fluid can be injected into the proximal end, through the cannula, and out of the distal end. The uninsulated electrode tip can include at least a portion of the distal end of the metal tubing. The sharpened tip end can include a bevel. The sharpened tip end can include a beveled portion of the metal tubing. The sharpened tip end can include at least in part a shaped portion of the distal end of the metal tubing. The shaped portion of the distal end of the metal tubing can include a tapered form of the metal tubing that converges to a tissue piercing tip end. The unitized high frequency electrode system can further include a flexible fluid carrying portion within the cannula.

The unitized high frequency electrode system can further include a unitized flexible leader including a single flexible tubing having at least one lumen channel within the single flexible tubing, the unitized flexible leader having a leader proximal end and a leader distal end, the leader distal end being connected to the proximal end so that the at least one lumen channel is connected to the proximal opening and an injection port that is connected to the leader proximal end and configured so that a fluid injected into the injection port passes through at least one lumen channel, through the proximal opening, through the cannula lumen, and out of the cannula lumen through the distal opening; and wherein the cannula has a lumen within the cannula that connects a proximal opening near the proximal end to a distal opening near the distal end. The leader distal end can be inseparably connected to the proximal end. The electrical connection can be connected to the leader proximal end and can be adapted to connect to a high frequency generator. The single flexible tubing can further include a plastic tubing having an inner lumen configured so that fluid injected into the injection port passes through the inner lumen and through the cannula lumen to exit the cannula through the distal opening. The temperature connection and the high frequency electrical connection can include wires that pass within the inner lumen of the plastic tubing. The high frequency electrical connection and the temperature connection can further include wires that are at least in part imbedded into the wall of the single flexible tubing.

The single flexible tubing can further include a plastic tubing having a first inner lumen configured so that the fluid injected into the injection port passes through the inner lumen and through the cannula lumen to exit the cannula through the distal opening, and a second inner lumen which contains wires that are a part of the high frequency electrical connection and the temperature connection. The single flexible tubing between the leader distal end and the position of the injection port on the single flexible tubing can have a length in the range of about 0.2 to 2 inches. The single flexible tubing between the leader distal end and the position of the injection port on the single flexible tubing can have a length in the range of about 2 to 12 inches. The single flexible tubing between the leader distal end and the position of the injection port on the single flexible tubing can have a length in the range of about 12 to 20 inches. The single flexible tubing between the leader distal end and the position of the injection port on the single flexible tubing can have a length in the range of about 20 to 40 inches. The single flexible tubing between the leader distal end and the position of the injection port on the single flexible tubing can have a length in the range of about 40 to 400 inches. The cannula can further include a metal tubing, and the flexible leader further includes a single flexible plastic tubing, wherein the single flexible plastic tubing has a single lumen, the leader distal end being connected to the metal tubing, and the leader proximal end being connected to an electrical hub connection that connects the high frequency electrical connections and the temperature connection to a high frequency generator, and the leader proximal end connects the tubing lumen to the injection port. The leader proximal end can connect to a junction element that includes a fluid connection to the injection port and an electrical connection that connects the high frequency electrical connection and the temperature connection to a high frequency generator. The junction element can further include having a branch junction with a fluid branch that connects to the injection port and an electrical branch that connects to the high frequency electrical connection and the temperature connection. The injection port can further include a luer fitting. The injection port can further include a fluid coupling fitting.

The unitized high frequency electrode system can further include a single flexible leader having a leader proximal end and a leader distal end, the leader distal end being connected to the proximal end and an non-flexible injection port that is rigidly connected to the proximal end and configured so that fluid injected into the injection port passes through the proximal opening, through the cannula lumen, and out of the cannula lumen through the distal opening. The system can further include a hub that is rigidly connected to the proximal end of the cannula, the hub having a rigidly connected injection port, and the single flexible leader is connected to the hub. The single flexible leader can include an electrical hub connection at the leader proximal end, the electrical hub connection configured to connect the high frequency electrically connection and the temperature connection to a high frequency generator. The single flexible leader from the position of the connection between the leader distal end and the proximal end and the position of the electrically leader hub can have a length in the range of about 0.2 to 2 inches. The single flexible leader from the position of the connection between the leader distal end and the proximal end and the position of the electrically leader hub can have a length in the range of about 2 to 12 inches. The single flexible leader from the position of the connection between the leader distal end and the proximal end and the position of the electrically leader hub can have a length in the range of about 12 to 20 inches. The single flexible leader from the position of the connection between the leader distal end and the proximal end and the position of the electrically leader hub can have a length in the range of about 20 to 40 inches. The single flexible leader from the position of the connection between the leader distal end and the proximal end and the position of the electrically leader hub can have a length in the range of about 40 to 400 inches.

In another aspect, an injectable high frequency electrode system can include a cannula that includes a metal tubing, configured to be inserted into a patient's body and having a proximal end and a distal end, the distal end can include an uninsulated electrode tip. The system can include a fluid port connection to the proximal end configured so that fluid injected into the fluid port will pass through the cannula and exit out of the cannula near the distal end. The system can include a high frequency electrical connection located at least in part at the proximal end and configured so that a high frequency signal applied to the high frequency electrical connection will be connected to the uninsulated electrode tip. The system can include a temperature connection and a temperature sensor, the temperature sensor configured to be built into the uninsulated electrode tip to sense the temperature at the uninsulated electrode tip.

The uninsulated electrode tip can include at least a portion of the distal end of the metal tubing. The high frequency electrical connection and the temperature connection can include a flexible portion that is inseparably connected to the proximal end. The temperature connection can include a wire that runs in part through the interior space of the cannula and connects to the temperature sensor. The uninsulated electrode tip can include a sharpened tip end. The sharpened tip end can include a bevel or a beveled portion of the metal tubing. The sharpened tip end can include at least in part a shaped portion of the distal end of the metal tubing. The shaped portion of the distal end of the metal tubing can include a tapered forming of the metal tubing that converges to a tissue piercing tip end. The uninsulated electrode tip can include a metal tubing at its exterior surface, and the temperature sensor can be in thermal contact with the metal tubing to enable rapid temperature measurement of a target tissue adjacent to the uninsulated electrode tip. The metal tubing can be a diameter of at least 0.4 millimeters.

The system can further include an inseparable injection port connected to the proximal end, a fluid channel through the cannula, and a fluid exit channel at the distal end, whereby fluid can be injected into the injection port and pass through the fluid channel and out of the cannula through the fluid exit channel. The injection port can include a flexible fluid carrying portion. The flexible fluid carrying portion can include a flexible tubing portion containing at least one single channel lumen, the single channel lumen being fluid connected to the fluid channel and the injection port so that fluid injected into the injection port will pass through the single channel lumen and through the fluid channel to exit from the fluid channel exit, the single channel lumen housing at least a portion of the high frequency electrical connection and at least a portion of the temperature connection.

The high frequency electrical connection and the temperature connection can include a flexible leader portion that is inseparably connected to the proximal end and a unitized hub connection at the proximal end that is adapted to connect to a high frequency generator. The temperature connection can include a wire that runs in part through the interior space of the cannula and connects to the temperature sensor. The distal end of the cannula can include a curved portion to improve the positioning of the uninsulated electrode tip near the target tissue.

In a further aspect, an injectable high frequency electrode system can include a cannula having a proximal end and a distal end and a hub at the proximal end, and the cannula being configured to be inserted into a patient's body, and the cannula having an uninsulated electrode at the distal end. The system can include a probe adapted to be inserted into the cannula wherein the probe includes a temperature sensor, and a high frequency electrical connection configured so that a high frequency signal connected to the high frequency electrical connection can be connected to the uninsulated electrode, and so that the temperature sensor can sense temperature at the uninsulated electrode. The probe can have an injection port so that when the probe is inserted into the cannula and fluid is injected into the injection port, the fluid will pass through the cannula and out of the distal end. The cannula can be adapted so that fluid can be injected into the proximal end, through the cannula, and out of the distal end into a target tissue of the patient's body near the distal end of the cannula. Fluid injected into an injection port can pass through the cannula and exit out of the distal end when the probe is inserted into the cannula and coupled to the hub. The cannula can include an injection port that is inseparably and flexibly connected to the proximal end and a fluid channel from the port through the cannula to the distal end so that fluid injected into the port will exit out of a distal opening at the distal end. The port further includes a flexible tubing inseparably connected to the hub, and an inner lumen of the flexible tubing that connects to an inner lumen of the cannula wherein the inner lumen of the cannula connects to the distal opening. The injection port can include a flexible fluid carrying portion. The flexible fluid carrying portion can include a flexible tubing portion containing at least one single channel lumen, the single channel lumen being fluid connected to the fluid channel and the injection port so that fluid injected into the injection port will pass through the single channel lumen and through the fluid channel to exit from the fluid channel exit, the single channel lumen housing at least a portion of the high frequency electrical connection and at least a portion of the temperature connection.

In another aspect, a method for treating neural structures can include percutaneously inserting a self-supporting electrode system through the skin and target tissue of a patient's body. The self-supporting electrode system can include a unitized high frequency electrode system that includes a cannula configured to be inserted into a patient's body and having a proximal end and a distal end. The distal end can include an uninsulated electrode tip, a high frequency electrical connection that is inseparably connected to the proximal end and configured so that a high frequency signal connected to the high frequency electrical connection will connect the high frequency signal to the uninsulated electrode tip, and a temperature connection and a temperature sensor. The temperature sensor can be configured to be inseparably built into and in thermal contact with the uninsulated electrode tip and the temperature connection can be inseparably connected to the proximal end and connected to the temperature sensor, so that a temperature readout apparatus connected to the temperature connection can read the temperature at the temperature sensor. The method for treating neural structures can further include connecting the high frequency connection to a high frequency generator, and applying the signal output from the high frequency generator through the high frequency connection to the uninsulated electrode tip; and connecting a temperature readout apparatus to the temperature connection and reading the temperature at the temperature sensor.

The metal tubing can be insulated over at least a portion of its surface. The uninsulated electrode tip can have a sharpened point formed by a beveled portion of the metal tubing. The cannula can be rigidly adapted to be capable of self-supported penetration of skin and tissue near spinal nerves and bones.

The method of treating neural structures can include identifying the position of a nerve related to a spinal facet joint and inserting the unitized high frequency electrode into the patient's body so that the uninsulated electrode tip is near the position of a nerve. The method of treating neural structures can include identifying the position of a dorsal root ganglion and inserting the unitized high frequency electrode into the patient's body so that the uninsulated electrode tip is near the dorsal root ganglion. The method of treating neural structures can include identifying the position of an inter-vertebral disc and inserting the unitized high frequency electrode into the patient's body so that the uninsulated electrode tip is within the inter-vertebral disc. The method of treating neural structures can include identifying the position of a neural structure and inserting the unitized high frequency electrode into the patient's body so that the uninsulated electrode tip is near to the position of the neural structure.

The electrode system can further include a fluid port connection that is inseparably connected to the proximal end and the connection can be configured so that fluid injected into the fluid port will pass through the cannula and exit out of the cannula near the distal end. The method of treating neural structures can further include injecting a therapeutic fluid into the fluid port connection so that the therapeutic fluid will infiltrate a target tissue near the uninsulated electrode tip.

The details of one or more embodiments of the invention are set forth in the accompanying drawings and the description below. Other features, objects, and advantages of the invention will be apparent from the description and drawings, and from the claims.

DESCRIPTION OF DRAWINGS

In the drawings which constitute a part of the specification, embodiments exhibiting various forms and features hereof are set forth, specifically:

FIG. 11 shows a process for application of an integral, rigid, tissue-piercing RF cannula with beveled tubing point and built-in temperature sensor.

Like reference symbols in the various drawings indicate like elements.

DETAILED DESCRIPTION

Figure 1:
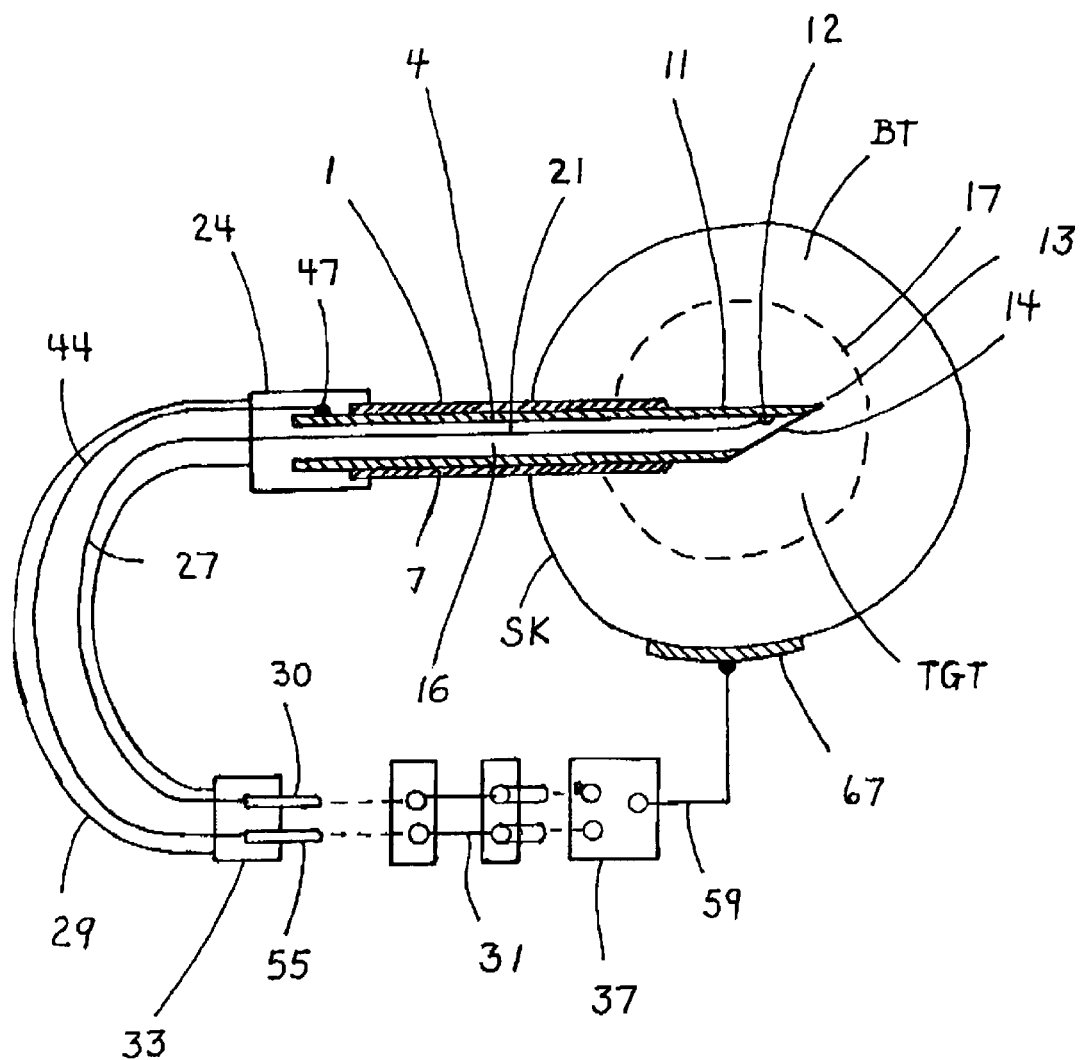
FIG. 1 is a schematic diagram showing a system with an integral high frequency electrode in sectional view having flexible leader connections.

Referring to FIG. 1, electrode 1, shown in sectional view, includes a rigid tubing 4 that is insulated by insulation 7 over a portion of its surface. Tubing 4 has an uninsulated electrode tip 11 at its distal end. Its distal end has a sharpened point 12 and a sharpened bevel shape 14 at its distal-most tip. In one example, the tubing can be metal tubing such as stainless steel tubing. In one example, the interior space 26 of the tubing 4 can be unfilled. In another example, the interior space 26 can be filled with, for example, epoxy or other material. At the uninsulated electrode tip, there is a temperature sensor 12 that is in thermal contact with the uninsulated electrode tip so that during high frequency application, the temperature sensor will measure the temperature of the target tissue near the tip. A temperature connection includes a wire or several wires, indicated schematically by the connection 21 that connects at the distal end to temperature sensor 12, and connects at the proximal end to an external flexible portion 27 that connects further to a connection plug 30. A flexible electrical connection wire 44 connects the tubing 4 to high frequency plug 55. In another example, the plugs 30 and 55 plug into an intermediate cable 31 which in turn can connect to high frequency generator 37. As an example of an intermediate connection cable, the C112-TC cable of Radionics, Inc., is used to connect Radionics RF electrodes to the RFG-3C generator of Radionics, Inc. High frequency generator 37 supplies high frequency signal output through wire 44 to conductive tubing 4, and thus to uninsulated electrode tip 11. High frequency generator 37 also reads out the temperature from temperature sensor 12 so that the temperature of target tissue can be monitored during the high frequency application. At the distal end of tubing 4, there is a hub 24 that provides a grip for the clinician to push the electrode into tissue TGT. In one example, the hub at proximal end of tubing 4 can be closed to fluids so that no fluids can be injected into the interior space 26 of cannula 4 and no fluid can be injected into the target tissue TGT through the distal end opening in the bevel 14.

Referring to FIG. 1, the hub 24 can be made of for example, plastic and bonded to the proximal end of tubing 4 to mechanically fix it and to secure the connections 27 and 44 so that they will not separate under use and manipulation of the procedure. The flexible connections 44 and 27 can be either separate wires or enclosed in a flexible tubular enclosure such as schematically illustrated element 29. Tubing 29 can, for example, be plastic tubing such as PVC, silicone, or materials. In one example, the structure including flexible elements 27, 44, and 29 can be considered to be a leader structure or a leader connection that integrally contains the components for convenience and efficiency of handling. At the proximal end of the leader element, in one example, there can be a hub 33 that contains or encloses the connection elements 30 and 55 and other pin or plug connections that can be part of the leader connection structure. In one example, there can be three or more wires in the leader element, such as for example, a copper, constantan, a high frequency signal output wire, and ground or bipolar wire, all contained within the leader jacket 29. Tubing 29 can be secured to hub 24 to prevent it from separating during use and also to provide a strain relief for wires 44 and 27 which can experience bending stress as they emerge from the end of hub 24. In one example, the hub can be sealed so that no fluid can enter the lumen of tubing 4. In one example, there is no fluid access at or near the proximal end of electrode 1 or the leader connection 29. The inner space 16 of the tubing 4 can be sealed and/or filled with a medium such as epoxy so that liquids or gases cannot communicate with the inner space to inhibit transmission of fluids or gases into the patient's body when electrode 1 is inserted into the patient's body. This has the advantage of reducing the risk of infection and contamination of the bodily tissues during the electrode placement during the clinical procedure and the manipulation of the electrode 1 as it is pushed through the skin on its path to the target In some clinical situations there is no requirement to inject fluid into the target tissue.

In those situations, the electrode system can be simplified by not having an injection port or injection access. In the example of FIG. 1, the electrode system does not have an injection port or injection access. This has an advantage that it reduces the expense to make the electrode. Another advantage is that it reduces the complication of mechanical structure of the electrode system, and reduces weight and encumbrance of the system to the clinician during its application. Another advantage of the unitized construction of the electrode system of FIG. 1 is that it simplifies the number and complexity of the electrode components the clinician must deal with during high frequency procedures in the treatment of the facet joint and dorsal root ganglion or other procedures. Because the electrode is one piece without separating elements, the number of separate steps and manipulations involved in performing the high frequency procedure is reduced. This has the advantage of reducing the price, reducing the complexity, and increasing the efficiency of the procedure. Another advantage is that there are also fewer component elements required for the hospital to purchase and hold in inventory, and that there are also fewer pieces that can be misplaced or fail during the procedure.

Another advantage of the electrode system of FIG. 1 is that the flexible leader connections 44, 27, and 29 result in less drag on the electrode system when it is placed at the target tissue. This reduces the chance that the proper positioning of the electrode will be lost during the procedure. Furthermore, the flexible extension wire connections will enable the connection plugs 30 and 55 to be brought away from the site of the electrode in the patient body. Thus, the connection plugs will not be a source of interference or artifact during x-ray positioning and x-ray verification of the proper electrode positioning in the patient body which in the target tissue, are steps that are crucial to proper success of high frequency treatment of spinal nerves. It is a common practice to take x-ray images of the anatomy and of the electrode system in the direction that the cannula is pointing. In this situation it is an advantage to have a reduced amount of mass and material of the electrode system in the x-ray view. Thus, it is a further advantage to have the flexible extension connections such as elements 27 and 29 in the example of FIG. 1.

Referring to FIG. 1, the length of the shaft of electrode 1 can be determined to accommodate clinical needs such as the depth of the target tissue from the skin. For example, in the cervical region, the tubing 4 can have length in the range of 2 to 10 centimeters. In another example, in the thoracic, lumbar, or the sacral region, the tubing can be in the range of: 5 to 20 centimeters, or more depending on the patient's anatomy. The length of the exposed conductive tip 11 can be chosen to accommodate clinical needs. For example, for targets in the dorsal root ganglion, tip lengths of 1 to 5 millimeters or more are appropriate. For targets in the facet joints, tip lengths of 5 to 15 millimeters can be appropriate. In one example, the electrode of FIG. 1 can be percutaneously inserted into the inter-vertebral disc to perform high frequency therapy in that target tissue within the disc for the treatment of pain or for modification of the inter-vertebral disc material to treat pain or other discogenic disorders.

Referring to FIG. 1, the metal tubing 4 can be made of stainless steel. In another example, the tubing can be made of tungsten, or tantalum, or algeloy, or metal alloys of particular imaging or rigidly qualities to meet clinical needs. In another example, the tubing can be made of carbon fiber composites or be another advantage is that combination of metal and carbon fibers to suit imaging or rigidity needs. The insulation can be made of a variety of plastic or high dielectric and insulative layers. For example, the insulation can be made of Teflon, or polyurethane, or other well-known or specially formulated isolative tubings or insulative coatings. The insulation can be made in various thicknesses. In one example, the insulation can be in the range of thickness of 0.0005 to 0.003 inches.

Referring to FIG. 1, in one example, the thermocouple can be a copper and constantan. The element 21 can include a copper and a constantan wire, which are electrically connected at the thermocouple junction represented by element 12. The thermocouple junction 12 can be close to the inner wall of the metal tubing that is part of the uninsulated electrode tip 11 so that there is close thermal contact to the tip 11 and so that it will give an accurate reading of target tissue temperature during high frequency treatment. In another example, the thermocouple junction 12 can be at the external surface of the electrode tip, as for example, at the margin of the bevel 14. This will give a rapid and accurate temperature reading of target tissue temperature. In another example, the thermocouple junction can be made of stainless steel and constantan. For example, the element 21 can include a constantan wire that is electrically fused or connected to the stainless steel wall of the uninsulated electrode tip 511, as for example, represented by the element 12. In one example, the thermocouple junction 12 can be formed by welding, or soldering, or electrically gluing, or in some other way electrically connecting the constantan wire 21 to a portion of the tubing at the tip 11.

Referring to FIG. 1, a connection wire 59 connects the high frequency generator 37 to reference electrode 67 that is in contact with the skin SK of the living body. This completes the electrical circuit for the high frequency generator so that RF current will flow through the patient's body. For example, the reference electrode 67 can be a ground plate electrode, as illustrated by the reference element offered by Radionics, Inc.

Figure 2:
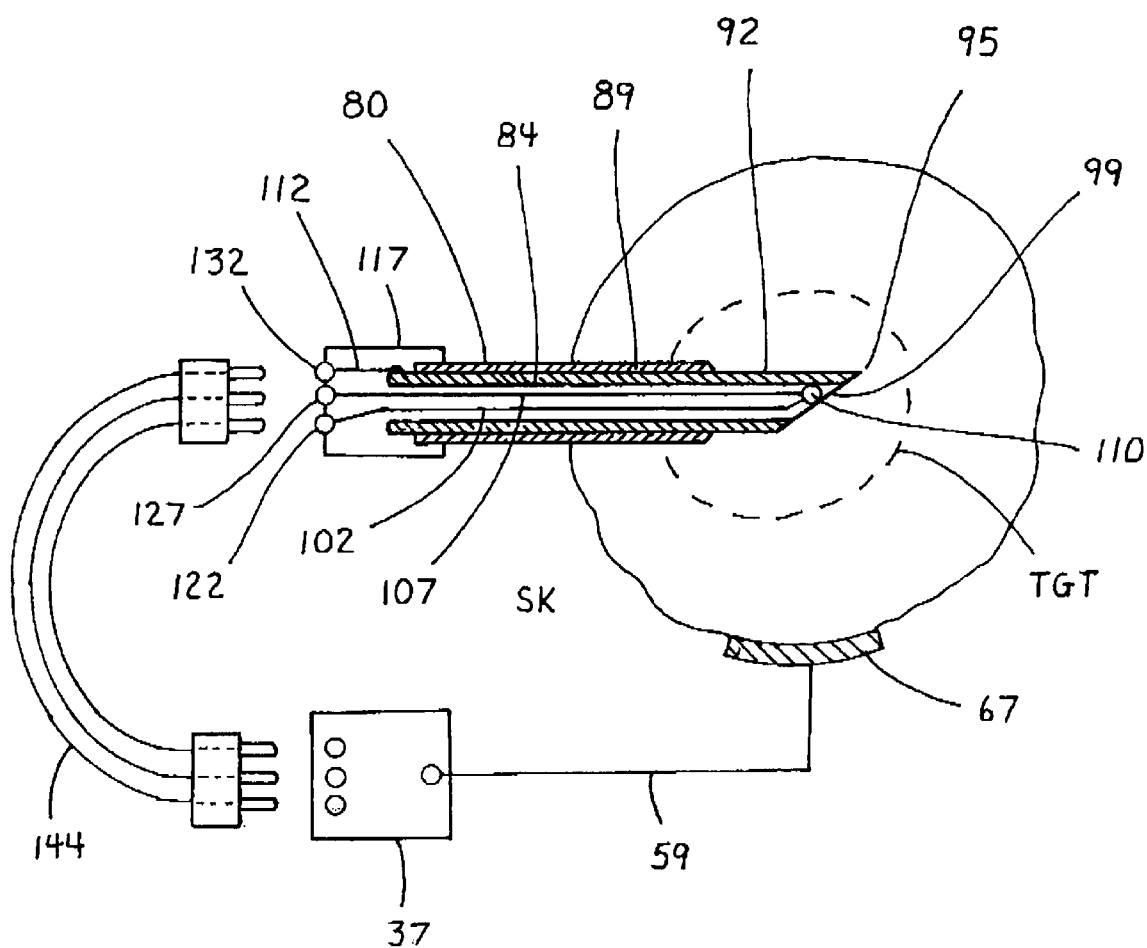
FIG. 2 is a schematic diagram showing a system with an integral high frequency electrode in sectional view having fixed hub connections.

Referring to FIG. 2, a high frequency electrode 80, shown in sectional view, includes a rigid tubing 84. In one example, the rigid tubing can be made of stainless steel or other suitable metal to suit clinical needs. The rigid tubing shaft can be insulated by insulation 89 over its length except for the uninsulated electrode tip 92 at the distal tip of the electrode. The distal tip can be sharpened to a point 95 by, in one example, grinding the rigid tubing to a bevel, or to multiple bevels, as illustrated by the bevel line 99. A TC junction 110 can be located at the uninsulated electrode tip In one example, the thermocouple junction can be an electrical fusion of two dissimilar metal wires 102 and 107. The TC junction can be in close contact with the inner wall of the metal tubing that includes the distal tip 92 for good thermal contact with the uninsulated electrode tip wall and thus to provide thermal good contact with the target tissue the is just outside the tip. In another example, the thermocouple junction 110 can be positioned near the bevel margin 99 so that it is in contact with the target tissue when the electrode is inserted into the patient's body. One advantage is that the temperature sensor, represented by the TC junction, is in good thermal contact with the target tissue. Therefore, the temperature readings will be fast and accurate, and this will improve the accuracy and the safety of the clinical procedure.

Referring to FIG. 2, the TC connections 102 and 107 connect to contacts 122 and 127, respectively, that is rigidly built into the hub 117. The high frequency connection to the electrode, and thus to the uninsulated electrode tip, can be made by the wire 112. It connects to the proximal end of the metal tubing 84, and also connects to a contact 132 that is rigidly connected to the hub 117. The metal tubing 84 can be of sufficient diameter and wall thickness that it is sufficiently rigid and robust to allow controlled, percutaneous, self-supported insertion of the electrode, without need for a guide needle, through the skin SK and the tissue near, for example, the spine of the patient's body, so that that the uninsulated electrode tip can be controlled and positioned to the desired target tissue TGT. The electrode can be electrically connected to a high frequency generator 31 by the connection cable element, schematically shown as 144, that plugs into the hub contacts 122, 127, and 132. In one example, the unit 144 can be composite of multiple wires and a jacket to cover them, such as a plastic insulative covering. In one example, the contacts 122, 127, and 132 can be fixed rigidly to the hub 117. In one example, there can be only two hub contacts, if for example, there is only one high frequency connection wire such as 112, and one thermocouple wire such as 127, which can be, for example, a constantan wire that is fused to the metal tubing wall at the thermocouple junction 110. In another example, there can be three contacts such as 122, 127, and 132 as illustrated in the FIG. 2. For example, there can be a copper wire 102 to 122, a constantan wire 107 to 127, and a high frequency connection wire 112 to 132 that also connects to the metal tubing 84 at the distal end of the tubing. In one example, the thermocouple junction 110 can be a fusion of the copper and constantan wires. The high frequency generator 37 can be a source of high frequency and stimulation signal outputs of the electrode, and can also include temperature readout apparatus to read out the temperature at the electrode tip 92 during the clinical procedure.

Figure 3:
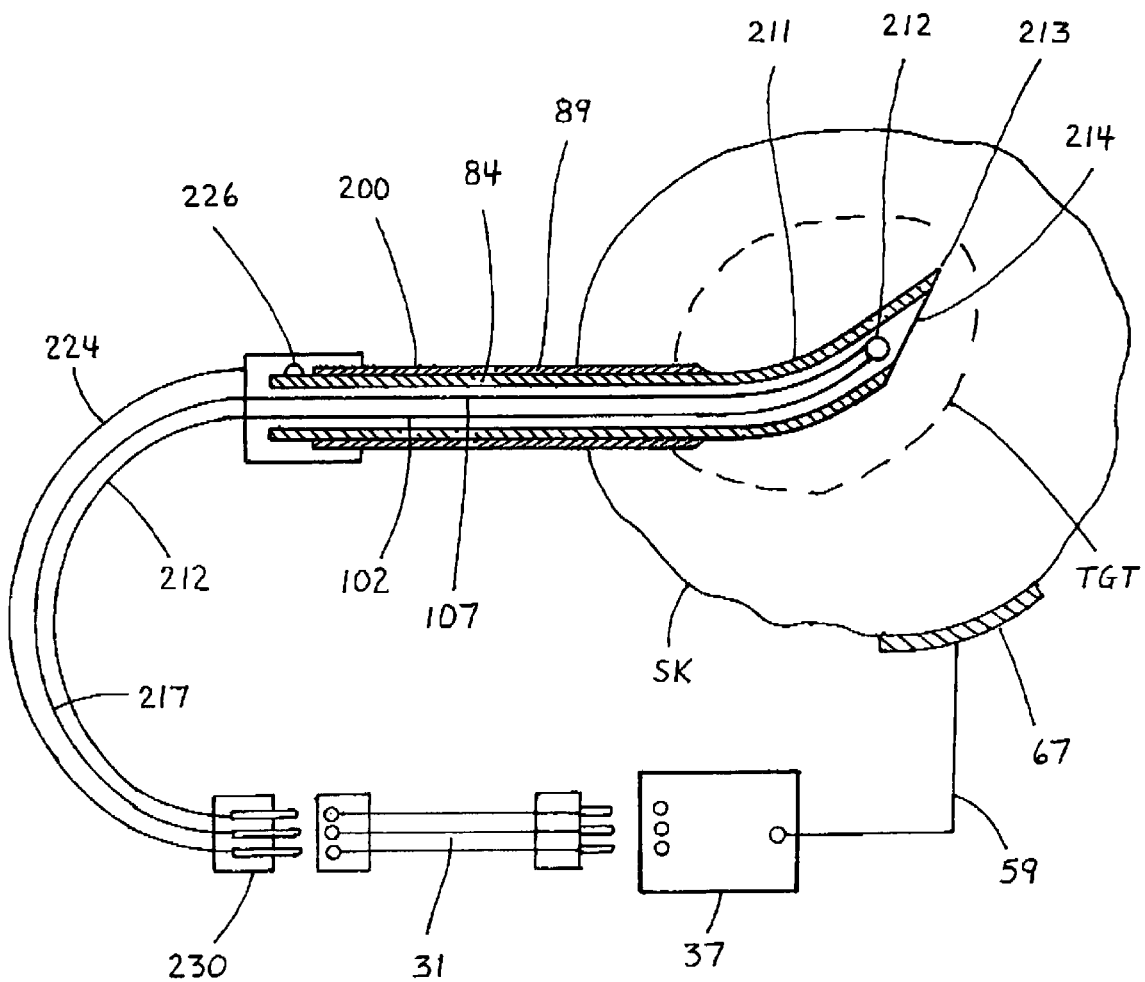
FIG. 3 is a schematic diagram showing a system with an integral high frequency electrode in sectional view having a curved distal tip and flexible leader connections.

Another example of a unitized electrode 200 is shown in a sectional view in FIG. 3. Tubing 84 can be insulated by insulation 89, except for the distal end, which is an uninsulated electrode tip 211. The distal end of the electrode has a curved shape, so that the distal tip 211 is of the axis of the electrode shaft 84. One advantage of the curved electrode is that during insertion through the tissue of the patient's body towards the target tissue, the electrode can be steered by twisting and turning the shaft and curved tip, resulting in a steering effect as the electrode is advanced. Another advantage is that the curved distal tip can be laid parallel to spinal nerve or other structure so that the surface of the uninsulated electrode tip contacts the target tissue to be treated over a longer range. Another advantage is that the curved tip can be positioned at a more oblique angle to a spinal nerve, so that the pointed tip approaches the spinal nerve at more normal direction. This can be useful in some clinical situations.

Referring to FIG. 3, a temperature sensor 212 can be located inside the distal tip and very close to, or against the inside wall of the metal tubing that is part of the external structure of the tip. An advantage is that the thermal contact to the uninsulated electrode tip, and thus of the tissue just outside the tip, is very good, providing fast and accurate temperature readings during the high frequency treatment. The temperature sensor can be, for example, a TC junction. The two wires 102 and 107 can be for example, copper and constantan, or can be some other combination of dissimilar metals. The thermocouple junction 212 can be fused, welded, thermally glued, or otherwise thermally bonded to the wall of the curved portion 211 of the distal end of the metal tubing 84.

Referring to FIG. 3, at the proximal end of the tubing shaft 84, a flexible wire 224 makes an electrical connection at junction 226 to the metal tubing 84, which in turn provides an electrical connection to the uninsulated electrode tip 211. Wires 212 and 217 are flexible and connect to the TC wires 102 and 107, respectively. The wires 224, 212, and 217 are connected the connector 230, that in turn can connect to the intermediate cable 31. Cable 31 can plug into the high frequency generator 37 that provides signal outputs and temperature readout. The flexible leader system including 212, 217, and 224 has the advantage that it provides a strain relief of the electrical connections from the electrode to the high frequency generator. Another advantage is that the flexible leader element reduces the tugging forces on the electrode when it positioned in the patient's body so that the risk of movement of the electrode from its correct position at the target position is reduced.

Figure 4:
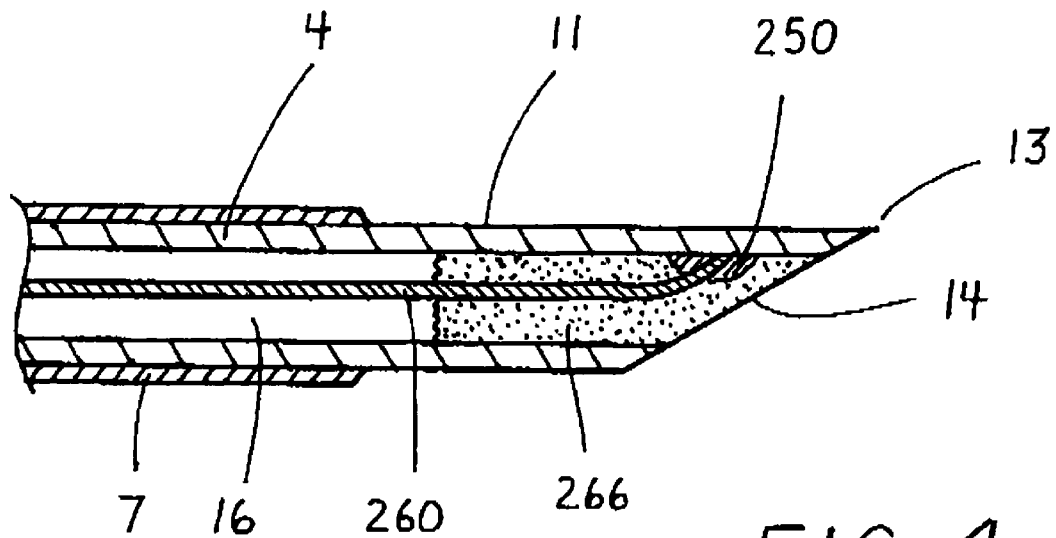
FIG. 4 is a schematic diagram showing an electrode's distal tip in sectional view with beveled metal tubing tip and fused TC connection to the tubing wall.

Referring to FIG. 4, a sectional, schematic view is shown of an electrode distal end. This example could be, for example, the distal tip of the electrodes shown in FIGS. 1, 2, and 3. The rigid tubing 4 can be, for example, a metal tubing, and insulation 7 can insulate the shaft of the electrode except for the uninsulated electrode tip 11. In one example, the pointed tip 13 of the distal end of the electrode tip can be made by grinding the metal tubing 4 at its distal end to a bevel, illustrated by distal surface 14. The tubing 4 can have an inner space 16 that can be filled with material, or, alternatively, can remain empty of solid material. In one example, as illustrated in FIG. 4, the inner space of the tubing 4 at its distal end can be filled with a material 226, which can be for example, epoxy, glue, plastic, or some other non-metallic material. In another example, the material 266 can be a metal or metallic filler, such as, for example, stainless steel welded in place, solder, metal filled epoxy, conductive cement, brazing material, and other materials to suit constructional or clinical objectives. In one example, the metal tubing 4 itself, at its distal end, does not close the lumen of the tubing. The metal tubing can be beveled to form at least a portion of the pointed tip of the electrode. One advantage of this is that it is simple to grind the metal tubing to make a beveled point. Another advantage is that by grinding the metal tubing to a point, leaving the lumen unclosed, the inner space of the distal end can be filled with material of the makers choosing. In one example, epoxy that can be loaded with radio opaque material, such as tantalum or tungsten powder, can be used to fill the inner space of the distal tip. One advantage of this is that the electrode tip can be better visualized under x-ray imaging, so that during positioning of the electrode at the target position, the clinician can better judge the tip position. Another advantage is that by leaving the lumen unclosed by the tubing itself, the position the temperature sensor at the tip can controlled and confirmed during manufacture.

Referring to FIG. 4, in one example, a TC wire 260, such as constantan, can be passed into the inner space 16 of the tubing 4, and the wire 260 can be fused to the inside of the tubing wall at the uninsulated electrode tip 11. This can be done during manufacturing by visualizing the wire 260 through the opening at the region of the bevel 14, and then welding, soldering, or conductively gluing the wire to the metal tubing wall, as illustrated by the junction 250. Another advantage is that this makes assembly of the thermocouple junction simple and inspectable, which improves the quality and the reliability of the temperature sensor. In another example, the element can represent two TC wires, such as for example, a copper and a constantan wire that are insulated from each other and which are fused electrically a the thermocouple junction represented by element 250.

Figure 5:
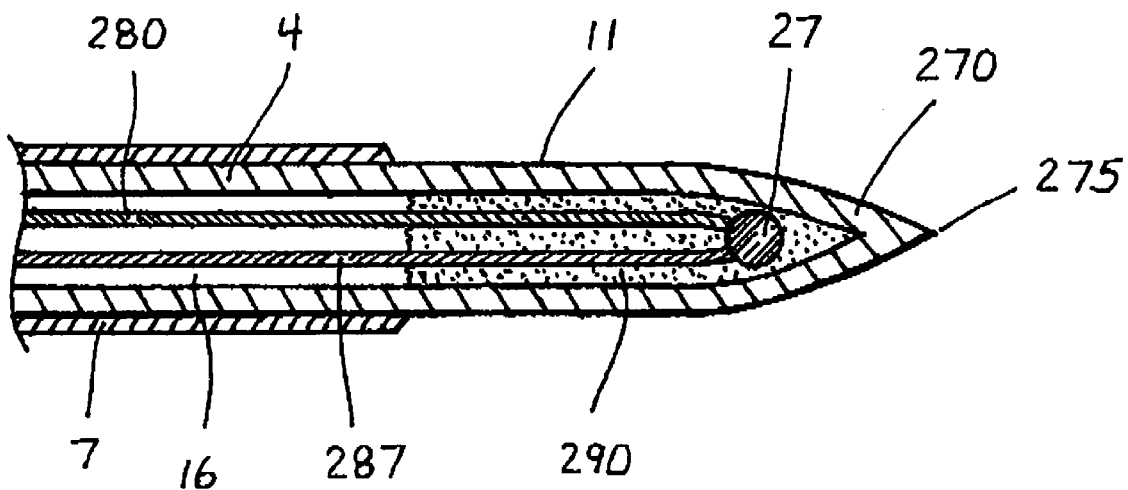
FIG. 5 is a schematic diagram showing an electrode's distal tip in sectional view with closed metal point and indwelling bimetal TC junction.

Referring to FIG. 5, another example of an electrode tip end is shown in sectional view. The metal tubing 4 continues into the uninsulated electrode tip 11. In one example, at the distal most tip, the metal tubing can be shaped to a conical point region that ends at a sharp pointed end 275. In another example, the distal portion of the metal tubing 4 can be tapered down to a convergent form, such as for example, a cone shape or a more rounded convergent shape. In one example, the convergent point can be a very sharp point, such as for example, the point of a sewing needle. In another example, the point can be less sharp and have a small radiused nose at the very distal tip, as for example, a radius of 0.0005 to 0.0004 inches. In the inner space 16 of the tubing, there are two TC wires 280 and 287 that can be for example, copper and constantan. The TC wires can be fused into a thermocouple junction 27 that is positioned at the inside and distal end of the tip 11. The thermocouple junction can be positioned in direct thermal contact with the inner walls of the conical point for close and accurate temperature measurements of target tissue during high frequency therapy. In one example, there can be a radio opaque material 290 filling the inside of the tip to enhance visualization of the distal tip under x-ray imaging during the procedure. The radio opaque material could be a high-density material such as tantalum, tungsten, barium sulphate, or other high atomic number material that can be installed inside the tip.

Figure 6:
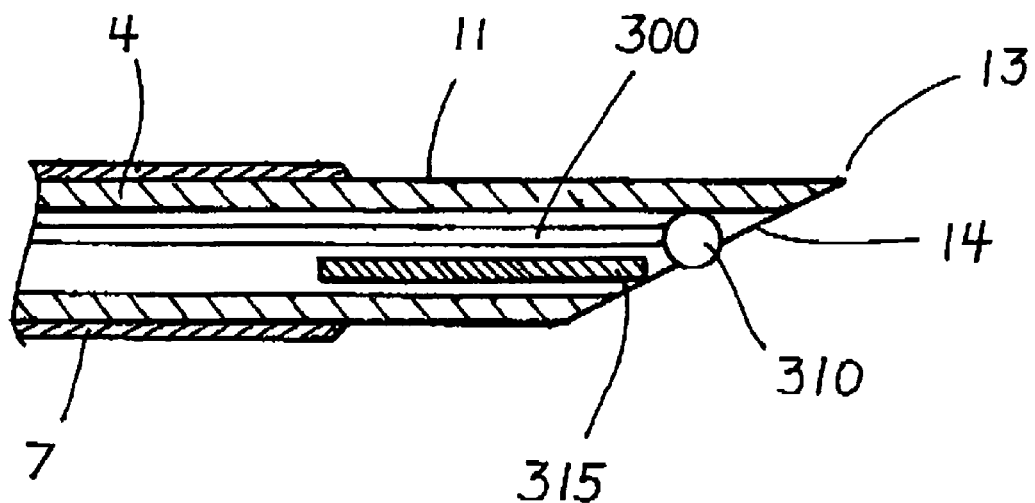
FIG. 6 is a schematic diagram showing an electrode's distal tip in sectional view with beveled metal tubing tip, TC junction, and radio opaque marker.

Referring to FIG. 6, another example of an electrode tip end is shown in sectional view. As in FIG. 4, the distal tip includes a beveled end of the metal tubing 4 that is part of the shaft of the electrode. The very distal end can be unclosed by the metal tubing. An element 300 runs inside the tubing and includes temperature sensor connections. At the distal end, element 300 connects to a temperature sensor 310. In one example, element 300 can be one or more TC wires, and element 310 can be a thermocouple junction. For example, element 300 can be a copper and a constantan wire. In another example, element 300 can be a constantan wire that is welded or fused to the metal tubing wall at a junction 310. The thermocouple junction 310 can be in contact with, or fused to, the wall of the tubing at the uninsulated electrode tip 11 for good thermal contact. In one example, shown schematically in FIG. 6, the temperature sensor can be flush with, or even extend out beyond the margin 14 of the bevel, so that the TC is part of the external surface of the distal tip itself. One advantage of this is that the thermocouple junction 310 is in direct contact with the tissue near the tip during a procedure. Another advantage is that the temperature sensor will be in intimate thermal contact with the target tissue, so that good control of a high frequency heating treatment can be achieved. Element 315 can be a radio opaque element that is positioned inside the lumen of the metal tubing tip. For example, it can be a section or segment of high-density wire, such as for example, tungsten or tantalum wire that is bonded inside the metal tubing at the distal tip. In one example, the element 315 can have the same length as the uninsulated electrode tip 11 so that in an x-ray view, it can represent the position of the tip in the target tissue. One advantage of this is that it will increase visualization of the electrode tip during x-ray guidance.

Figure 7:
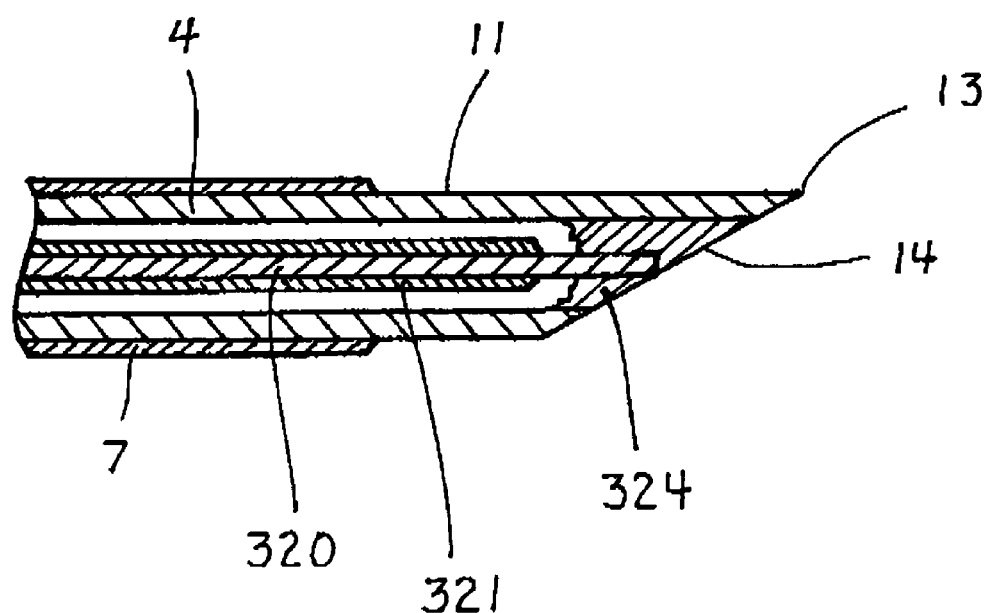
FIG. 7 is a schematic diagram showing an electrode's distal tip in sectional view with beveled metal tubing tip and TC connection fused with the tubing occlusion.

Referring to FIG. 7, another example of an electrode tip end is shown in sectional view. As in FIG. 4, the distal tip includes a beveled end of the metal tubing 4 that is part of the shaft of the electrode. An element 320 that runs inside the tubing and includes temperature sensor connections. For example, element 320 can be a constantan wire, that is insulated over its length by insulation 321 so that it does not electrically contact the inner wall of the metal tubing 4. At its distal end, wire 320 it can be uninsulated, and it can be electrically connected to the distal end of the metal tubing, as illustrated by the junction material 324, to form a thermocouple junction at 324. In another example, the element 320 can be two thermocouple wires that are insulated from each other and, for example, from the tubing 4, and they can be conductively fused at the joint 324 to form a thermocouple junction. In one example, material 324 can represent a welded joint of the stainless steel metal tubing wall and the constantan wire 320. In one example, the junction 324 can be a solder joint that bonds the wire 324 with the tubing 4 to form a thermocouple junction. In one example, the joint can be volumetric-filling, so that it closes and occludes the end lumen of the metal tubing at the tip end. In another example, the joint does not fill or occlude the distal end lumen of tubing 4. In another example, the joint can be a conductive epoxy that can be loaded electrode a radio opaque material for improved x-ray imaging.

Figure 8:
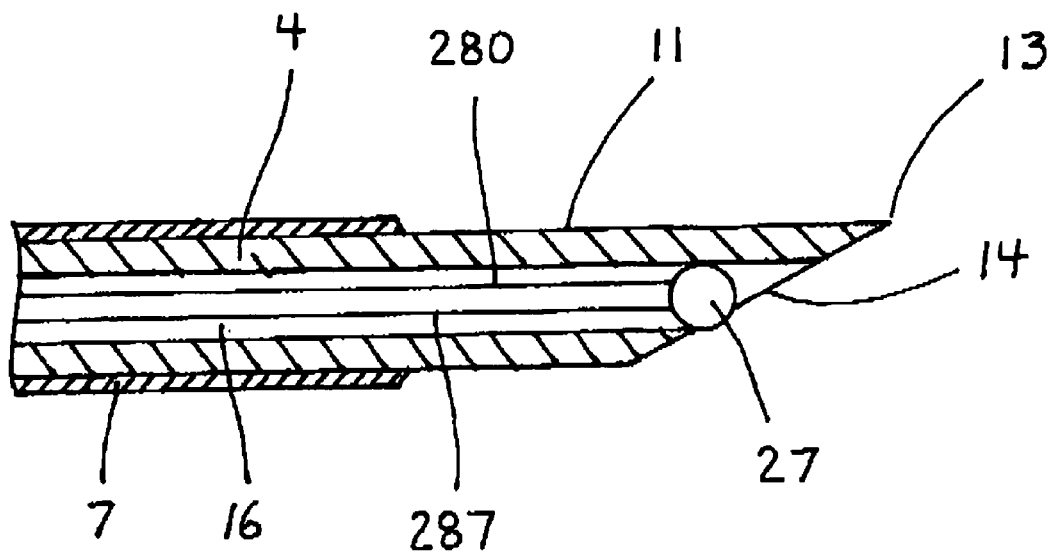
FIG. 8 is a schematic diagram showing an electrode's distal tip in sectional view with beveled metal tubing tip and TC junction occluding the tubing lumen.

Referring to FIG. 8, another example of an electrode tip end is shown in a sectional view. As in FIG. 4, the distal tip includes a beveled end of the metal tubing 4 that is part of the shaft of the electrode. The very distal end is not closed by the metal tubing. Elements 280 and 287 can be TC wires that run inside the tubing and can include temperature sensor connections. At the distal end, elements 280 and 287 are electrical wires connected to a thermocouple junction 27. For example, TC wires 280 and 287 can be copper and constantan wires, that are insulated from each other. They can be welded or fused together to form the junction 27. The thermocouple junction can be in contact with, or fused to, the wall of the tubing at the uninsulated electrode tip for good thermal contact. In one example, the temperature sensor can be flush with, or even extend out beyond the margin 14 of the bevel, so that the TC is part of the external surface of the distal tip itself. In one example, the thermocouple junction 27 can actually occlude all of, or most of, the open lumen of the distal end of the metal tubing 4 so that the thermocouple junction is part of the external surface of the distal tip. One advantage of this is that the thermocouple junction is in direct contact with the tissue near the tip during a procedure. Another advantage is that the temperature sensor will be in intimate thermal contact with the target tissue, so that good control of a high frequency heating treatment can be achieved. Another advantage is that, where the distal end is occluded; tissue will not accumulate in the lumen of the electrode cannula and can be passed on into the target tissue. This can be important in some clinical situations, such as when the electrode is placed into the intervertebral disc, because any tissue that is dragged into the inter-vertebral disc by the electrode can increase the risk of infection and discitis.

Figure 9:
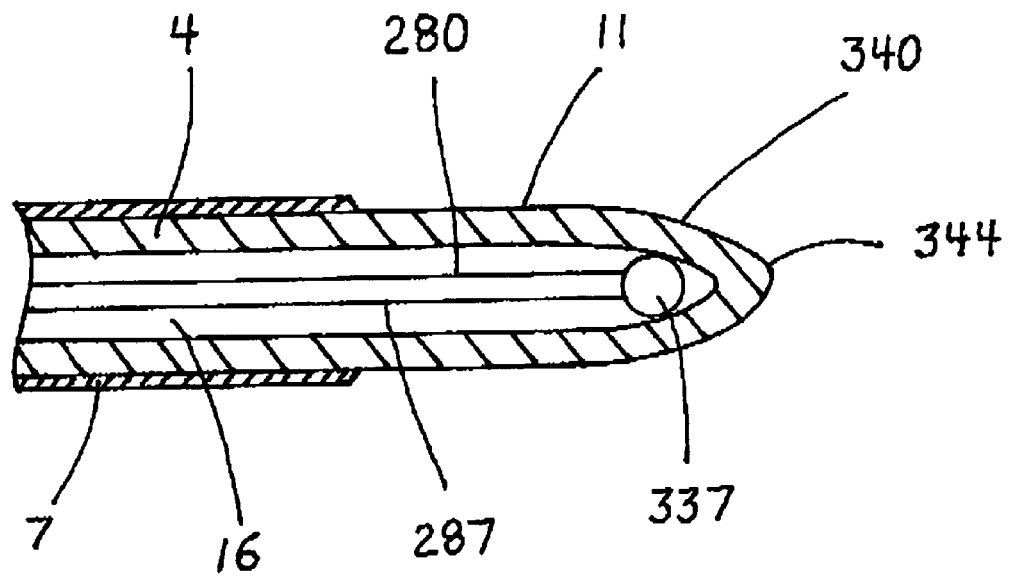
FIG. 9 is a schematic diagram showing an electrode's distal tip in sectional view with closed semi-sharp metal point and indwelling bimetal TC junction.

Referring to FIG. 9, another example of an electrode tip end is shown in sectional view. The metal tubing 4, which is insulated of a portion of its shaft length, can continue into the uninsulated electrode tip 11. At the distal-most tip, the metal tubing can be shaped to a tapered portion 340 that ends at its distal extremity in the shape that is not sharpened to a point, but rather semi-rounded. In one example, the shape of the nose 344 can be a bullet nose. In another example, the shape of the nose 344 can be conical with a radius at the distal tip in the range of for example, 0.1 to 0.7 millimeters. For example, a radius of 0.1 to 0.3 millimeters can be sufficiently so that the electrode can be pushed through skin and tissue to be directed to target tissue near the spinal nerve. In the inner space 16 of the tubing, there can be, in one example, two TC wires 280 and 287 that can be, for example, copper and constantan. In another example, the two TC wires can be replaced by one wire, for example, a constantan wire that can be fused to the electrode wall near distal end 340 or 344 to provide a stainless steel and constantan thermocouple junction. In one example, two TC wires can be fused into a thermocouple junction 27 that is positioned at the inside and distal end of the tip 11 near the distal end 344. The thermocouple junction can be positioned in direct thermal contact with the inner walls of the distal end of the electrode for close and accurate temperature measurements of target tissue during high frequency therapy. In one example, there can be a radio opaque material (not shown in FIG. 9) inside of the tip to enhance visualization of the distal tip under x-ray imaging during the procedure. The radio opaque material could be a high-density material such as tantalum, tungsten, barium sulphate, or other high atomic number material that can be installed inside the tip. The high-density material can be, for example, in powder form and mixed with epoxy, so that it can be injected into the electrode distal end.

Figure 10:
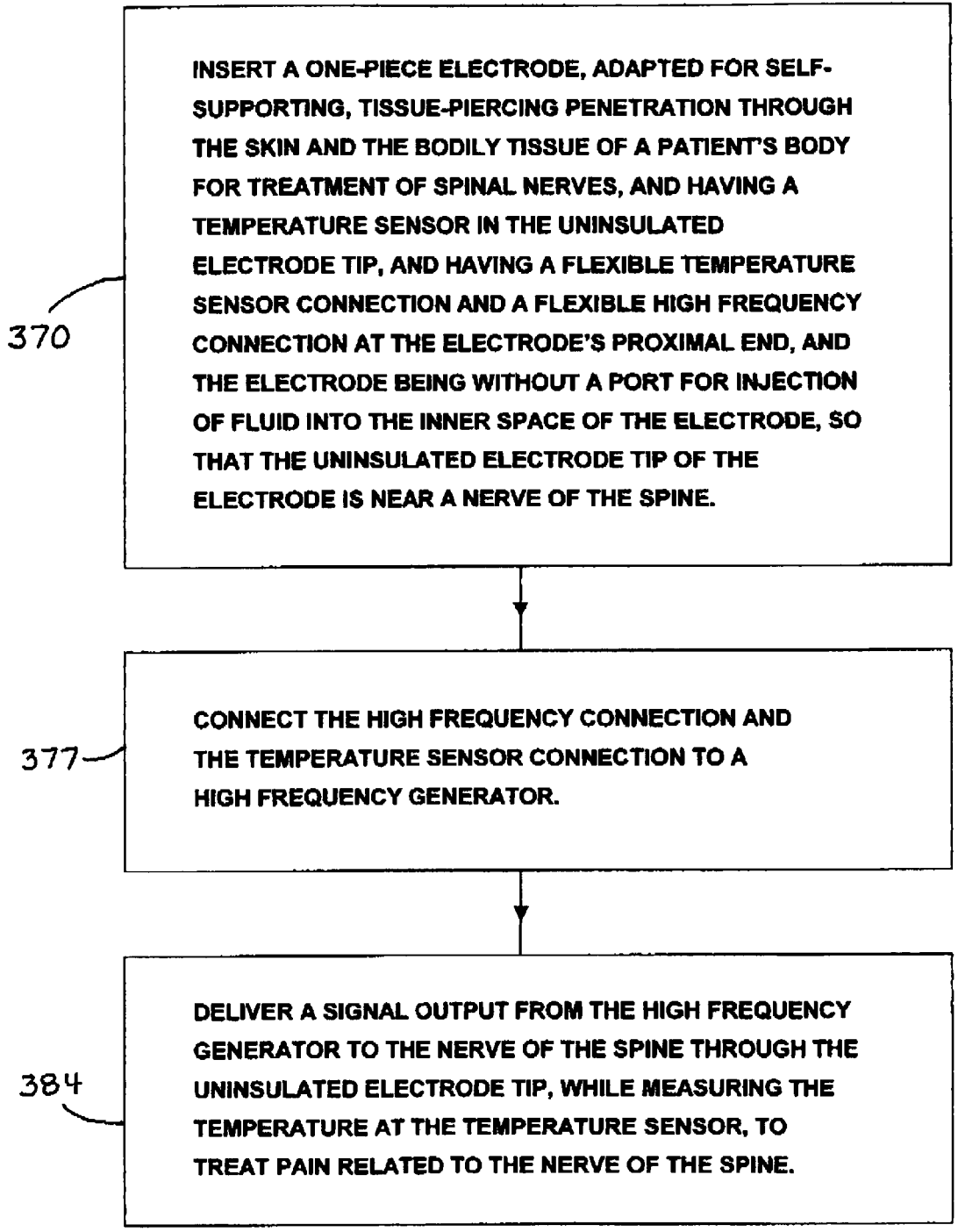
FIG. 10 shows a process for application of an integral, self-supported tissue piercing RF cannula with built-in temperature sensor and no fluid port.

Referring to FIG. 10, the operation of the system and method is shown with a flow diagram. A unitized (one-piece) electrode, such as for example, the electrode system shown in FIGS. 1 and 3, can be inserted into the patient's body as indicated by block 370. In one example, the electrode has a sharpened distal tip and has sufficient strength and rigidity to be self-supported during the percutaneous insertion, so that the clinician can push the electrode, unsupported by, for example, a guide needle or other secondary device, through the skin and on into the target tissue of the patient's body near the spine (block 370). The electrode can be, in one example, a self-supported electrode adapted and configured to withstand that manipulation and to be sufficiently rigid to be directed, redirected, and steered through the tough tissues and bony obstacles near the spine so that the clinician can navigate the uninsulated electrode tip to the desired position near a spinal nerve or a dorsal root ganglion (block 370). In one example, the electrode can have a flexible leader element that includes a flexible wire connection for the temperature sensor and a flexible wire element for the high frequency connections (block), such as the example illustrated by the connection elements 44, 27, 30, and 55 shown in FIG. 1.

Referring to FIG. 10, block 377 indicates the step of connecting the electrode to a high frequency generator, which can be a source of high frequency or RF signal output, such as for example, the unit 37 in FIG. 1. In one example, the connection step of block 377 can include connecting flexible connections for the temperature sensor connection and the high frequency connection that are inseparably attached to the electrode system to the high frequency generator. In another example, the connection step of block 584 can include connecting flexible connections for the temperature sensor connection and the high frequency connection that are inseparably attached to the proximal end of the electrode system to an intermediary connection cable, such as for example the connection cable 31 in FIG. 1, that in turn connects to the high frequency generator. An example of such an intermediary connection cable is the C112-TC Cable of Radionics, Inc., Burlington, Mass. which is used to connect various RF electrodes to the Radionics RFG-3C or RFG-3C Plus radiofrequency generator.

Block 384 indicates the step of delivering the signal outputs of the high frequency generator to the electrode system through the high frequency connection and of monitoring temperature at the electrode tip by way of the temperature sensor connection. Step 384 can also include monitoring of other parameters associated with the electrode and the high frequency generator systems when the electrode is in the patient's body, such as monitoring tissue impedance and temperature. Block 384 can also include delivery of various signal outputs from the high frequency generator through the electrode system to the target tissue, such as stimulation voltage and current, and such as high frequency or RF voltage, current and power, either by a continuous or by a pulsed high frequency or RF waveform. Block 384 can also include monitoring the target tissue temperature during the delivery of the high frequency signal output to the target tissue in order to control the desired degree of heating of the spinal nerves or the dorsal root ganglia. In one example, block 384 can include treating a spinal nerve with high frequency signal output for treatment of a neurological problem associated with the spinal nerve including for example, relief of pain.

Referring to FIG. 11, the operation of the system and method is shown with a flow diagram. An electrode, such as for example, the electrode system shown in FIG. 2, can be inserted into the patient's body as indicated by block 400. In one example, the electrode has a sharpened distal tip and has sufficient strength and rigidity to be self-supported during the percutaneous insertion, so that the clinician can push the electrode, unsupported by, for example, a guide needle or other secondary device, through the skin and on into the target tissue of the patient's body near the spine (block 400). The electrode can be, in one example, a self-supported electrode adapted and configured to withstand that manipulation and to be sufficiently rigid to be directed, redirected, and the uninsulated electrode tip to the desired position near a spinal nerve or a dorsal root ganglion (block 400). The electrode including a shaft that includes rigid tubing, for example, stainless steel metal tubing, that extends to the region of the uninsulated electrode tip. In one example, the sharpened distal end of the tip can be made by beveling at least a portion of the metal tubing, as illustrated by the examples shown in the FIGS. 1, 2, 3, 4, 6, 7, and 8. In another example, the distal tip can be made by shaping the metal tubing at the distal end to a conical point, as for example, in FIG. 5. In another example, the distal tip can be made by shaping the metal tubing at the distal end to a semi-pointed conical configuration such as a bullet-shape, as for example in FIG. 9. In one example, the electrode can have a connection for the temperature sensor and a connection for the high frequency connections that are fixed to the proximal end of the electrode, as for example, illustrated by the connection elements 122, 127, and 132 at the proximal hub of the electrode shown in FIG. 2.

Referring to FIG. 11, the blocks 404 and 407 are analogous to the blocks 377 and 384 in FIG. 10, respectively, and represent the steps of connecting the high frequency generator to the electrode and of delivering signal output from the high frequency generator to the electrode to treat a neural structure.

Figure 12:
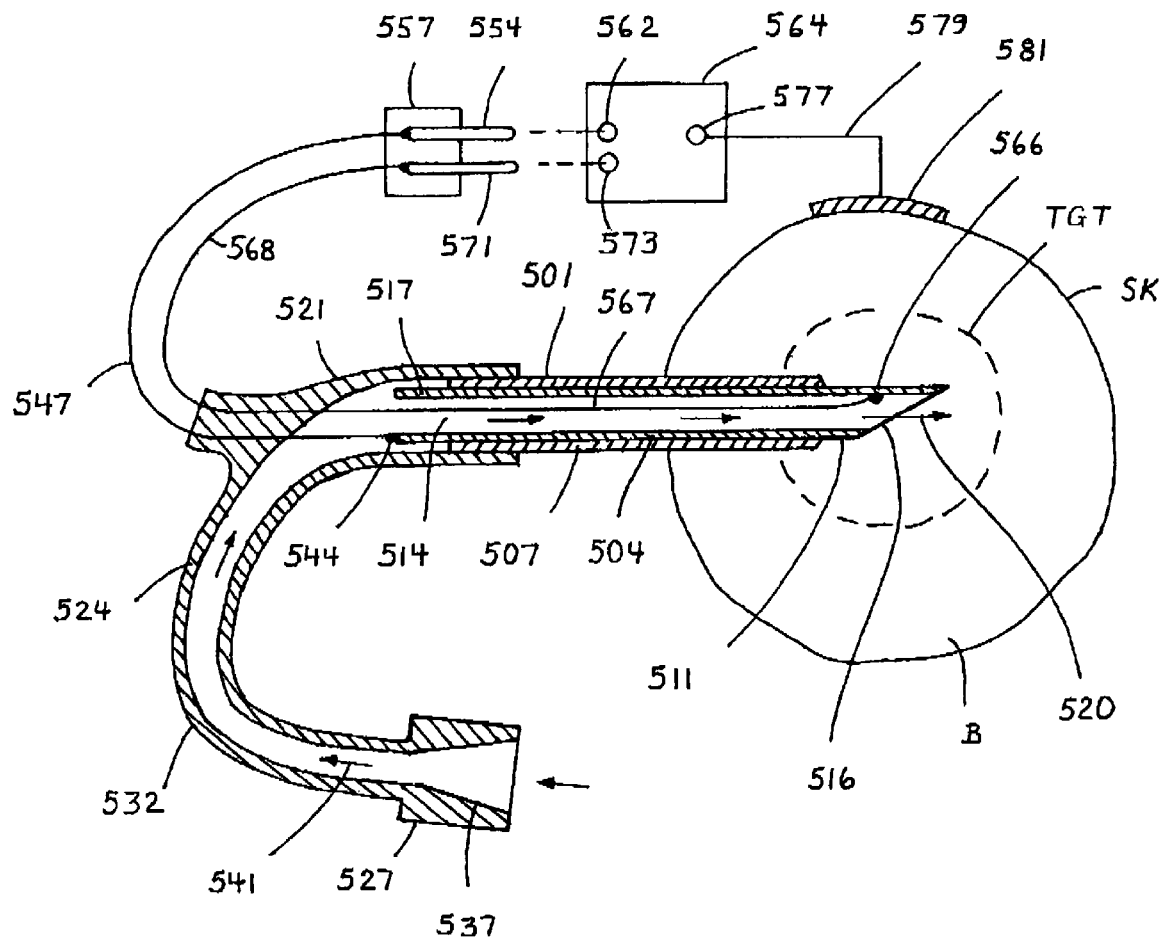
FIG. 12 is a schematic diagram showing a system with an integrated RF electrode including a needle having a flexible injection port, TC, and TC/RF connections.

Referring to FIG. 12, an integral, one-piece high frequency electrode includes a conductive metal tube 504 having an insulated coating 507 over a portion of its surface except for a conductive tip 511 at its distal end. The uninsulated electrode tip 511 can be sharpened to enable penetration into the patient's body and to place tip 511 in a desired target tissue TGT (viz. shown schematically as a dashed line). A coupling hub 521 attaches to proximal end 517 and merges with fluid coupling tube 524 that is coupled to an injection hub 527. Port injection of fluid into the electrode system can be done in a variety of configurations. In one example, the combination of hub 521, tube 524 and hub 527 can be an injection port 532 for port injection of fluid. Tube 524 can be a flexible plastic tubing, and hub 527 can have a luer taper fitting 537 to accept a fluid injector device such as a syringe (not shown). In one example, the injection port including units 521, 524, 532, and 527 can integrally and inseparably connect to cannula 501, and can facilitate injection of fluids, as indicated by the arrows such as, for example, 541. A lumen 514 inside tube 504 has a distal opening 516 at the distal end of the tip 511. Lumen 514 provides a fluid channel through the tubing 504 for fluid injected into port 537. The fluid can emerge out of the cannula at the distal end through the end lumen 516, as indicated by the arrow 520, enabling the fluid to infiltrate the target tissue TGT. For example, injection can include injection of contrast fluids, anesthetic fluids, saline fluids, or other fluids, before and during delivery of electric signals to tissue TGT. One advantage of the example of FIG. 12 is that fluid injection can be done without the need to couple or decouple ancillary or other separate elements or components to needle 501, thus avoiding delays and undesired movement of distal tip of the electrode in target tissue TGT.

Referring to FIG. 12, an electrical connection 544 of wire connector 547 to conductive metals tube 504 provide electrical connection of contact 554 on hub 557. Contact 554 can be connected to jack 562 on generator 564, so that signal outputs from unit 564, such as stimulation of RF electrical signals, can be carried through units 562, 554, 547, and 504 to the exposed tip 511 which exposes the signals from unit 564 to target tissue TGT. A thermal sensor 566 in tip 511 can be connected by wire 567 to connector wire 568 to contact 571 which can plug into jack 573 on generator 564. Sensor 566 can be a thermocouple (TC) sensor, such as, in one example, a copper-constantan junction or, in another example, a constantan wire 567 that is electrically fused to stainless steel tubing 504. Generator 564 can have temperature readout circuitry to measure the temperature a sensor 566 when RF output from unit 564 is delivered to tissue TGT. The combination of a TC sensor 566, connections 567 and 568, jack 751, tube 504, junction 544, connection 547, RF jack 554, and hub 557 in the example of FIG. 1 can be referred to as a TC/RF element and enable thermal sensing and signal output connection to the needle 501. Wires 547 and 567 can pass through hub 521, so that the TC/RF element is integrally and inseparably coupled to the needle 501 and to the fluid injection port as described herein.

One advantage of the example of FIG. 12 is that fluid injection, delivery of electrical signals, and temperature readout can be carried out during a procedure without coupling or decoupling injection elements or TC/RF elements to the needle element, thus saving time and inconvenience, and reducing the risk of movement of the needle tip 511 after it has been critically positioned in target tissue TGT.

Referring to FIG. 12, generator 564 can read impedance of tip 504 in tissue TGT, and readout and display the temperature at sensor 566. Unit 564 can have an electrical reference jack 577 that connects by wire 579 to reference electrode 581 that is in contact with the patient's skin SK.

The system of FIG. 12 can be used to treat spinal nerves to relieve pain. Tubing 504 can be 0.5 to 1.5 millimeters in outer diameter and 5 to 15 centimeters long or longer. The exposed tip can be 2 to 15 millimeters long, or longer. Tubing 537 can be plastic such as PVC, and in one example, can be of diameter 0.5 to 1.5 millimeters and can be flexible and lightweight. One advantage is that once the cannula 501 is placed in or near a spinal nerve or the dorsal root ganglion under x-ray control, there is no need to connect or disconnect the couplings for injection, temperature, or RF signal control. Connecting hubs 557 to an RF generator or hub 527 to a syringe will not disturb the needle 501 position TGT. This improves safety and efficiency. Another advantage is that this system of FIG. 12 is simple, easy and economical to make and packaged in a sterile packed, one-time use device.

Figure 13:
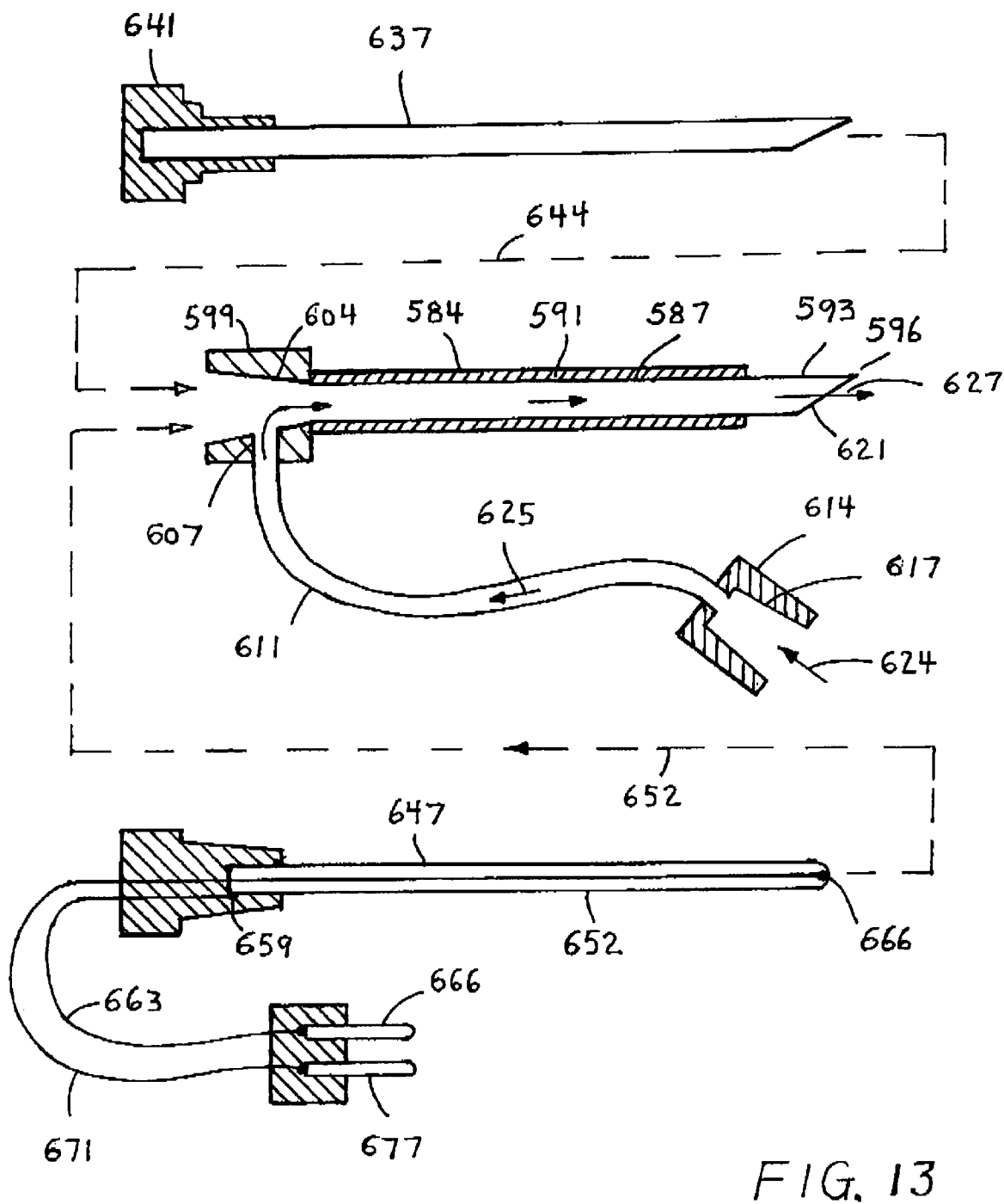
FIG. 13 is a schematic diagram showing a system with an insulated needle electrode with an integrated injection port, and a separate TC/RF element.

Referring to FIG. 13, a cannula 584 includes a metal tube that has insulation 591 on its surface except for exposed tip 593 that has point 596 for piercing tissue. Hub 599 connects to tubing 591 and has luer taper fitting 607 that is connected with flexible tubing 611 that connects to injection hub 614. Hub 614 can have a luer fitting 617 that can accept a syringe to enable fluid injection through the cannula 584 and out the distal opening 621 as indicated by arrows 624, 625, and 627. The fluid injection port including hole 607, flexible tube 611, and hub port 614 and 617 are integrally and inseparably connected to cannula 584.

In one example, a stylet 637 can be inserted into cannula 584 and hub 641 connected to hub 599 (indicated by dashed line 644). The assembly of cannula 584 and stylet 637 can be pushed into patient's tissue (not shown in FIG. 13). Fluid, such as anesthetic or contrast agent, can be injected into hub 614 to inject into tissue near lumen 621 for diagnostic purpose. The stylet 637 can be removed from cannula 584. The TC/RF element 647 can be inserted into cannula 584 (indicated by dashed line 652). The TC/RF electrode 647 can include a metal tubing. An electrical junction electrically connects tubing 652 and wire 663. Wire 663 connects to contact 666 that can connect to a signal output pack of generator (not shown in FIG. 13) to supply signal outputs to electrode element 647. Electrode 647 can in turn connect the signal outputs to exposed tip 593 by the electrical contact of electrode 147 to the inner walls of metal tube 87. The TC/RF electrode 647 has a thermal sensor 666, such as a thermocouple junction, which is connected by wire 671 to contact 677. Contact 677 can connect to a thermal sensor jack on a generator unit (not shown), and the generator can readout temperature measures by sensor 666. Sensor 666 can be positioned inside tip 593 and thus measure tissue temperature during application of RF output from the generator to target tissue. Fluid, such as saline, can be injected through cannula 584 when TC/RF element 647 in installed in cannula 584.

One advantage of the system in FIG. 13 is that saline fluid can be injected into target tissue when TC/RF element 647 is placed in cannula 584. Saline can, in some clinical situations, enhance the effectiveness on neural tissue of RF signal application in such procedures as RF pain therapy in the spinal nerves. The integrated, one-piece construction of the needle and injection port units in FIG. 13 eliminate the need to connect the injection port to the needle. This reduces time of coupling or decoupling elements. Another advantage is that flexible tubing 611 reduces mechanical disturbance of needle position in a delicate procedure. Once the cannula 584 with stylet 637 is in place and is inserted into the patient, the stylet can be removed and the TC/RF element 647 can be inserted directly into the cannula 584 without the need for any other separate element to be coupled to the cannula 584. This improves time, efficiency, and accuracy.

Figure 14:
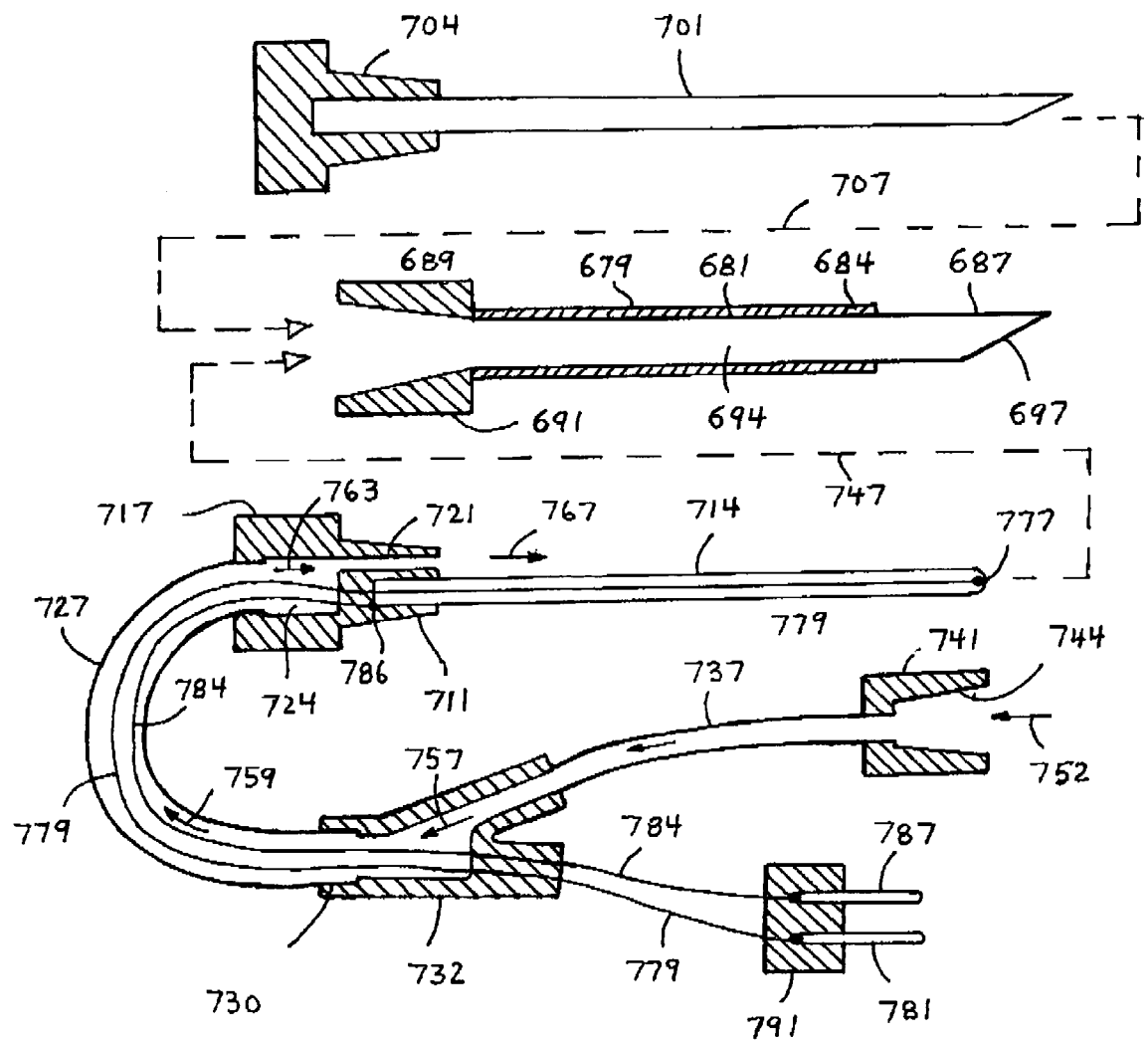
FIG. 14 is a schematic diagram showing a system with a needle electrode and a separate, integrated injection port and TC/RF element.

Referring to FIG. 14, a cannula 679 includes a metal tube 681 with insulation 684 on its surface except for exposed distal tip 687, and a hub 689 with luer connection fitting 691. Tubing 681 has lumen 694 that opens to distal opening 697. Stylet 701 has hub 704 that can be inserted into cannula 679, and hub 704 engages and can fluid-seal with hub 689. Stylet 701 inside cannula 679 can be pushed into the patient's tissue (not shown) so tip 687 is at a target tissue position. Stylet 701 can then be removed. Inject/TC/RF element 11 includes metal tube 714, which is fixed at its proximal end to hub 717. Flow hole 721 in the proximal end hub 717 opens into a space 724 inside hub 717. Flexible tubing 727 can be fluid sealed to hub 717 at the distal end of hub 717. Tubing 727 can be joined on its other end 730 to junction 732. Junction 732 can be joined to another flexible tubing 737 that is joined to a fluid port hub 741 that has a luer fitting 744. The Inject/TC/RF element 711 can be inserted into cannula 679 (indicated by dashed line 747) and the hub 717 can seal and/or lock to hub 689. Fluid injected into hub 741 by a syringe will cause fluid to flow as indicated by arrows 752, 757, 759, 763, and 767 and emerge from cannula distal opening 697 into the target tissue.

The electrode tube 714 has a thermal sensor 777 at its distal end, and sensor 777 can be a thermocouple (TC) junction. Wire 779 connects sensor 777 through tube 727 and junction 732 to contact 781. Wire 784 connects to tubing 714 at junction 786 and passes through tube 727, through junction 732 to connect to contact 787 and hub 791. Contact 781 can connect to a temperature sensing socket in a generator apparatus (not shown in FIG. 14) to readout temperature at sensor 777 which is within tip 687, and thus sensor 777 is measuring tissue temperature near tip 687. Contact 787 can connect to the signal output jack on a generator apparatus to deliver RF signal output through electrode 714 to the tip 687 by the contact of electrode 714 with the inner surface of metal tube 681.

One advantage of the example in FIG. 14 is that the integral, one-piece construction of the Injection/TC/RF element 711 enables the injection of fluid through cannula 679, the application of signal output to tissue cannula 679 and the application of signal output to tissue through tip 687 while measuring temperature of tip 687. These functions can be achieved without need to separately connect injection, TC, or RF function elements during the procedure. This reduces the time, steps, and manipulations in the procedure and reduces the risk of moving the position of tip 687 in target tissue.

In the examples of FIGS. 12, 13, and 14, the cannula can be made of stainless steel tubing with outer diameter in the range in millimeters of: 0.2 to 0.5; 0.5 to 1.0; 1.0 to 2.0; 2.0 to 3.0; or larger depending on clinical needles. Typical tubes for spinal nerve pain treatment are about 0.5 to 1.0 millimeters in diameter, and have lengths from 40 to 200 millimeters.

Tubing for the injection port can be plastic such as PVC, polyurethane, polyethylene, or other plastics. Insulation on the cannula can be coatings of Teflon or other common plastics and can have a thickness typically of 0.0005 to 0.020 inches or more depending on clinical needs.

Figure 15:
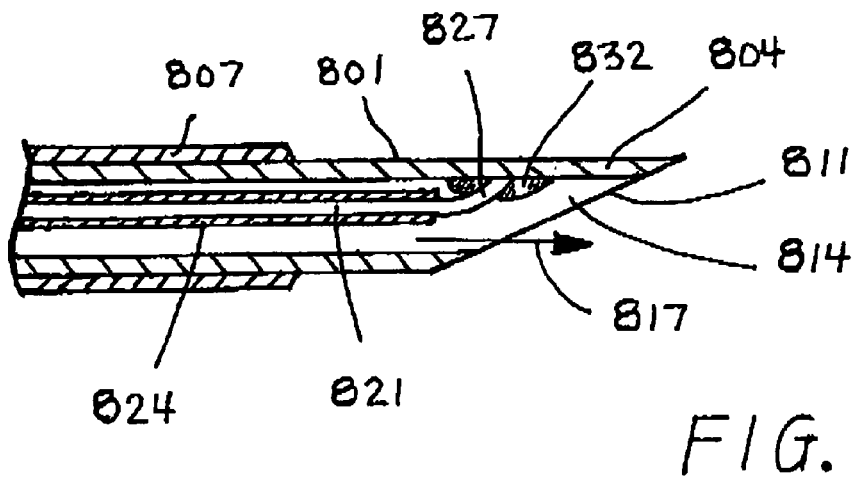
FIG. 15 is a schematic diagram showing the distal tip of an injectable needle electrode having an open lumen and a TC sensor fused to the metal wall of the tip.

Referring to FIG. 15, a sectional view of a cannula or needle tip 801 includes a metal tubing 804 that is exposed over tip 801. Insulation 807 covers the tubing 804 proximal to the tip 801. The tip 801 has a straight angular bevel point 811 and open lumen 814 for outflow of fluid from injection, indicated by arrow 817. Thermocouple 821 has insulation 824 over most of its surface except for the proximal portion 827 that is electrically connected to the inner surface of tubing 804, for example by welding, soldering, laser bonding, crimping, or other processes. In one example, wire 821 can be constantan. The thermocouple junction 832 enables temperature measurement of tissue near tip 801. Junction 801 can be constructed by the open access to wire end 827 and inner surface of tubing 804 at tip 804. One advantage of this example is that it provides rapid thermal monitoring at tip

801. Another advantage is that junction 832 can be made under visual control and open access. Another advantage is that it provides a rugged thermal sensor in a needle tip while allowing an open lumen for fluid injection.

Figure 16:
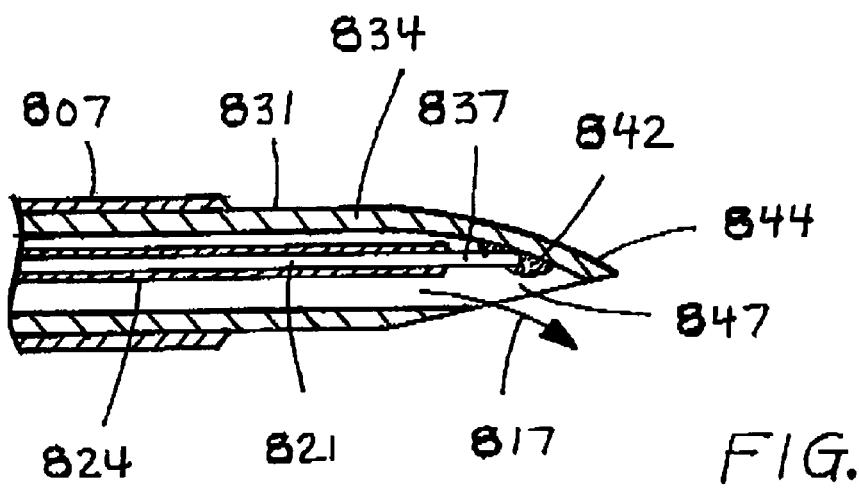
FIG. 16 is a schematic diagram showing the distal tip of an injectable needle electrode having an open lumen and a TC sensor fused to the metal wall of the tip.

Referring to FIG. 16, cannula or needle tip 831 includes metal tubing 334 and has a curved distal end 844. The distal lumen opening 847 faces more to the side than the example in FIG. 15. Units, with numbers 807, 821, 824, and 817 in FIGS. 15 and 16 are similar. Thermocouple wire end 837 forms a junction with tubing 384 on the inside of the curved portion 834. This has one advantage that wire 821 and joint 842 are less vulnerable to mechanical forces as the cannula is pushed through the patient's tissue. Another advantage is that wire 821 can be left straight and it naturally lies against the inner surface of curve tubing 844 during assembly to make it easier to produce the junction 842. Such a curved cannula tip shape can also be used, for example, in the embodiments related to FIGS. 1, 2, and 3 described above.

Figure 17:
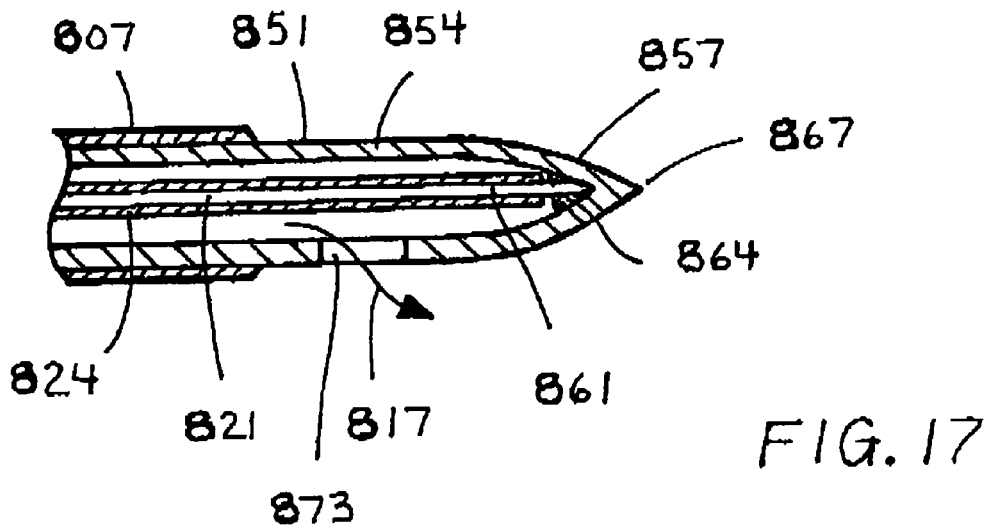
FIG. 17 is a schematic diagram showing the distal tip of an injectable needle electrode having a fluid side port and a TC sensor at the closed metal point of the tip.

Referring to FIG. 17, cannula with needle tip 851 includes tubing 854 which is formed at its distal end 857 to a conical or bullet shaped point. Sensor wire 821 can be welded or soldered to tip 857 in assembly to form the thermocouple junction 864. Point 867 can be later ground or polished to proper pointed shape. A side hole 873 enables outflow of injected fluid 817. One advantage is the junction is completely protected during tissue insertion. Another advantage is that outflow 817 in FIG. 17 can be directed to one side or another of the tip 851 depending on rotation angle of tubing 854.

In the examples FIGS. 1 through 17, thermocouple wire can be made from constantan, or from copper and constantan, or from iron and constantan, or from other combinations of dissimilar metal wires. The diameter of the thermocouple wire can be in the range of 0.0005 to 0.020 inches or larger depending on cannula tubing inner diameter and ease of use in assembly. Typical insulation on the thermocouple wire can be Teflon, polyethylene, or other dielectric materials.

Figure 18:
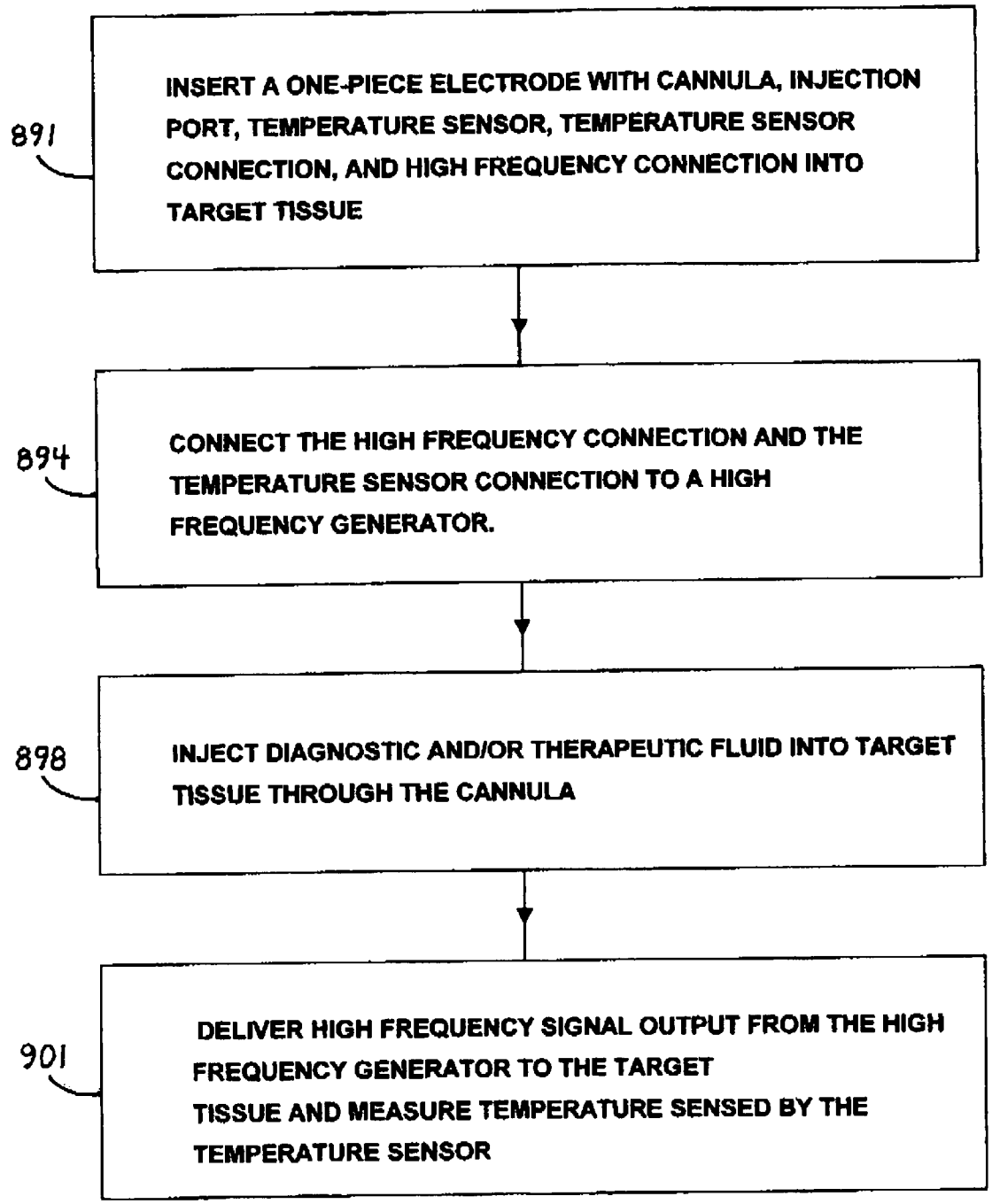
FIG. 18 shows a process for application of an integral system including a cannula, inject port, temperature sensor and RF connection.

Referring to FIG. 18, a process is shown includes a step 891 in which a one piece electrode includes a cannula, an injection port, a temperature sensor, and a signal connection is inserted into the patient so that the cannula tip is positioned in target tissue. In step 894 the temperature sensor is connected to an RF generator to readout temperature at the cannula tip, and the signal connection is connected to the RF generator to enable delivery of RF signal output to the exposed conductive tip of the cannula and thus to the target tissue. Injection of fluid through the injection port (step 898) can be done prior to or during delivery of RF output to the target tissue. In one example the fluid can be an anesthetic. In another example the fluid can be a contrast agent to enhance x-ray visualization of the cannula and tissue. In another example the fluid can be saline, which in some cases, such as RF ablation or Pulsed RF application spinal nerves, can enhance the effectiveness of the procedure by causing RF currents and electric fields to be better directed to the spinal nerve or to the dorsal root ganglion. In step 901, RF signal output is delivered to the target tissue through the cannula, and the tissue temperature is monitored by the temperature sensor to achieve a desired clinical result.

Figure 19:
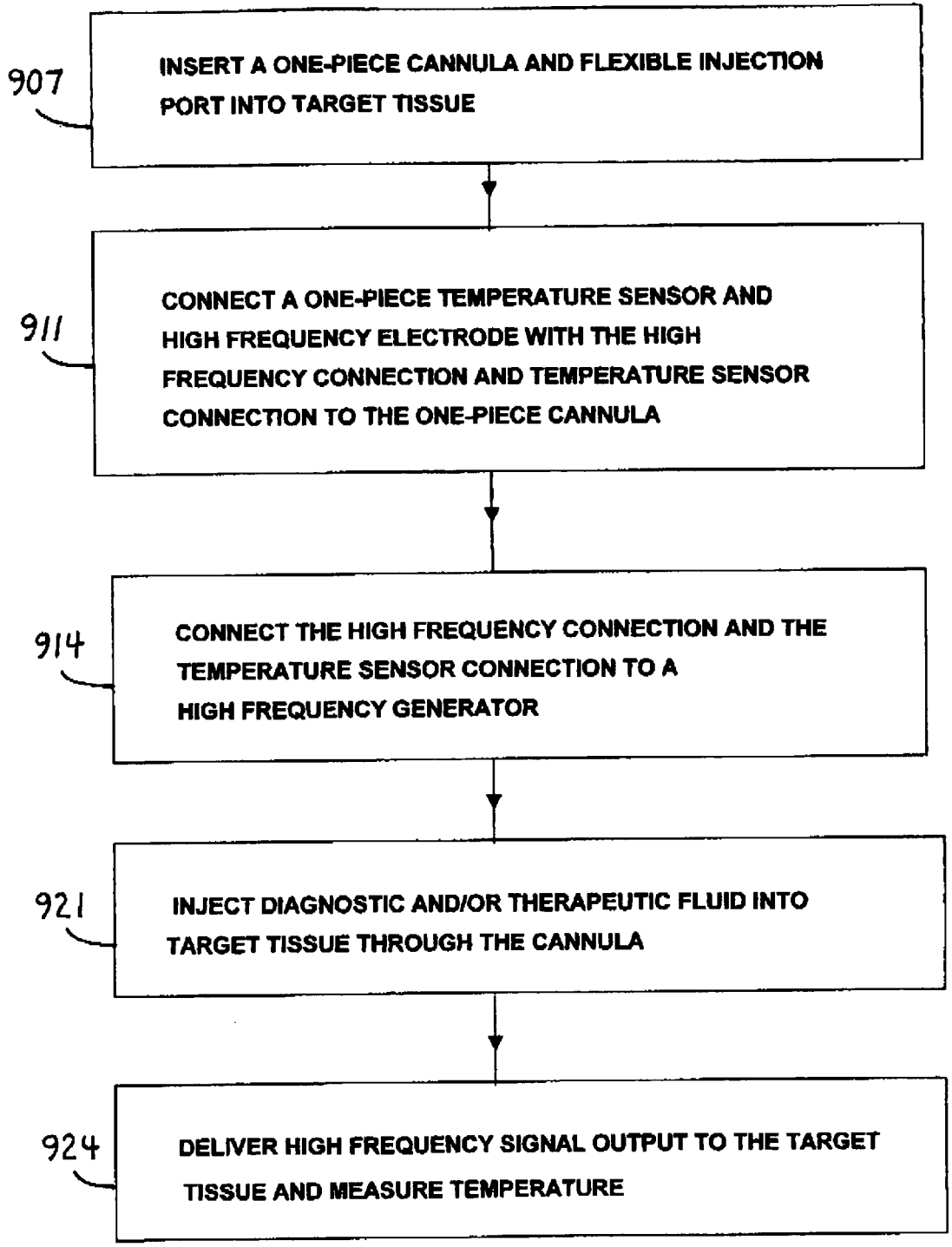
FIG. 19 shows a process for application of a system including an integral cannula with a flexible injection port and an integral temperature sensor and RF connection.

Referring to FIG. 19, the process includes inserting a one-piece electrode that includes a cannula with a flexible injection port into a patient so that the uninsulated electrode tip of the cannula is positioned in target tissue (step 907). A one-piece probe that includes a temperature sensor and a signal connection is connected to the one-piece electrode (step 908). Step 907 can include inserting the one-piece electrode with a stylet inside the cannula, and step 908 can include removal of the stylet before insertion of the one-piece probe into the one-piece electrode. The temperature sensor is connected to an RF generator, and the signal connection is connected to the RF generator (step 914). Fluid can be injected through the flexible injection port (step 921), preparatory to or during application of RF signal to the one-piece electrode. RF signal output from the RF generator can be delivered through the one-piece probe to the one-piece electrode tip and thereby to the target tissue (step 924). Step 924 can also include monitoring tissue temperature near the electrode tip by the temperature sensor to control the RF application procedure according to clinical indications.

Figure 20:
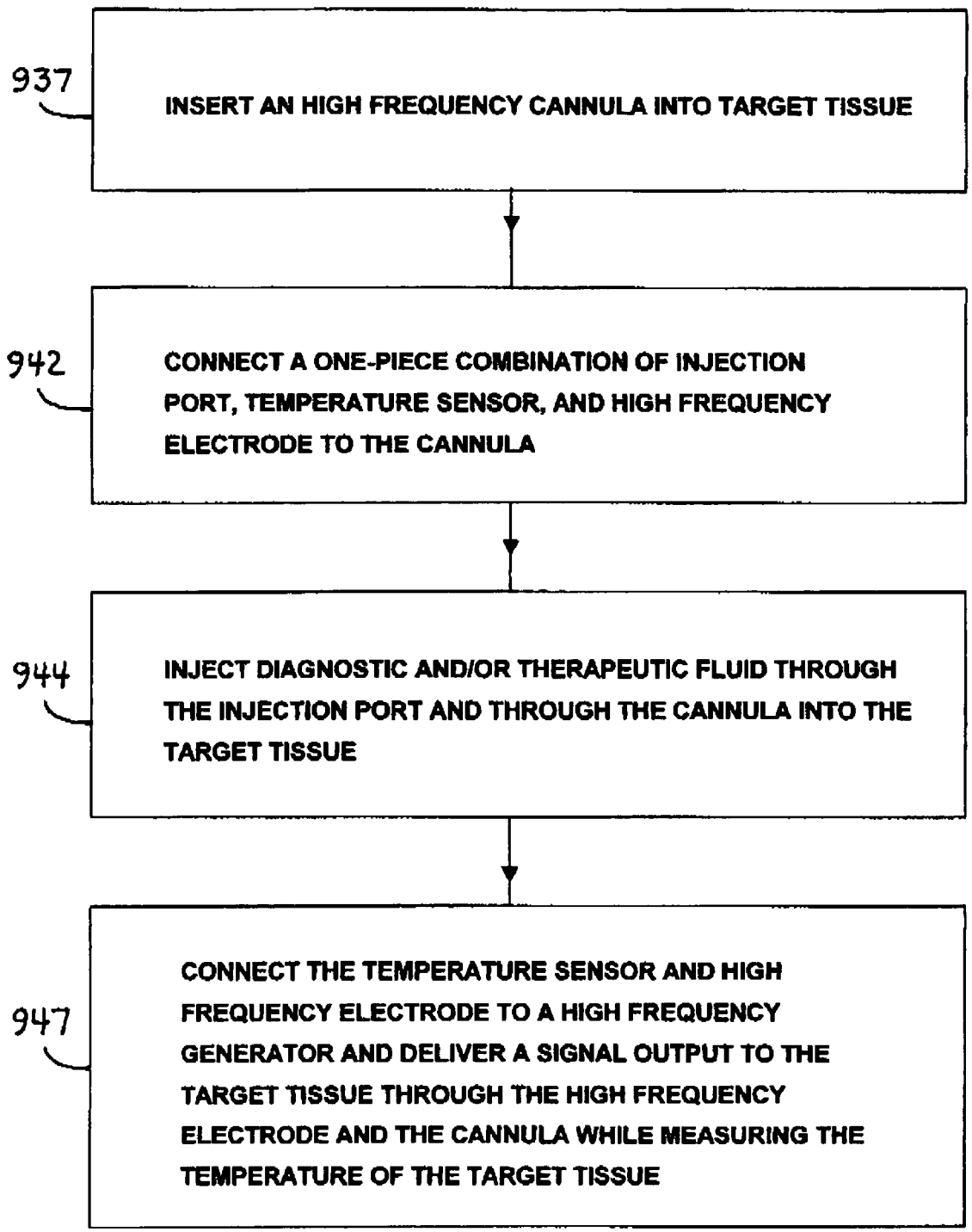
FIG. 20 shows a process for application of a system including a cannula and an integral combination of injection port, temperature sensor, and RF element.

Referring to FIG. 20, the process includes inserting a cannula into a patient, the cannula being insulated except for an exposed conductive tip, which is positioned in target tissue (step 937). An integral, or one-piece, probe including an injection port, a thermal sensor, and electrode with signal connector is inserted into the cannula (step 942). The electrode makes electrical connection to the conductive tip, and the probe is fluid sealed to the cannula. The injection port can be connected to a fluid source, for example a syringe, and fluid can be injected into the one-piece probe so that the fluid emerges at a distal opening at the cannula's tip to infuse into the target tissue (step 944). The temperature sensor and electrode are connected to an RF generator, and RF generator signal output is applied to the target tissue through the conductive tip (step 947). The target tissue temperature can be read-out by the RF generator during the RF signal application.

In the methods illustrated by FIGS. 10, 11, 18, 19, and 20, and in the examples of the systems shown in the other figures herein, the electrode system, or the element that is part of the electrode system, that is described as one-piece can also be referred to as being unitized or as having a unitized construction in which the elements or components that constitute the one-piece unit are inseparably united in a one-piece unit. For example, the electrode systems of FIGS. 1, 2, 3, and 12 can be described as one-piece, or equivalently, unitized. They can include various combinations of component elements, depending on the specific configuration of the example shown in the particular figure, including, for example: tubing in the shaft portion, temperature sensors, temperature sensor leader wires, high frequency leader wires, temperature sensor and high frequency connections, and fluid ports, that are built-in together and inseparably connected into the electrode system.

Figure 21:
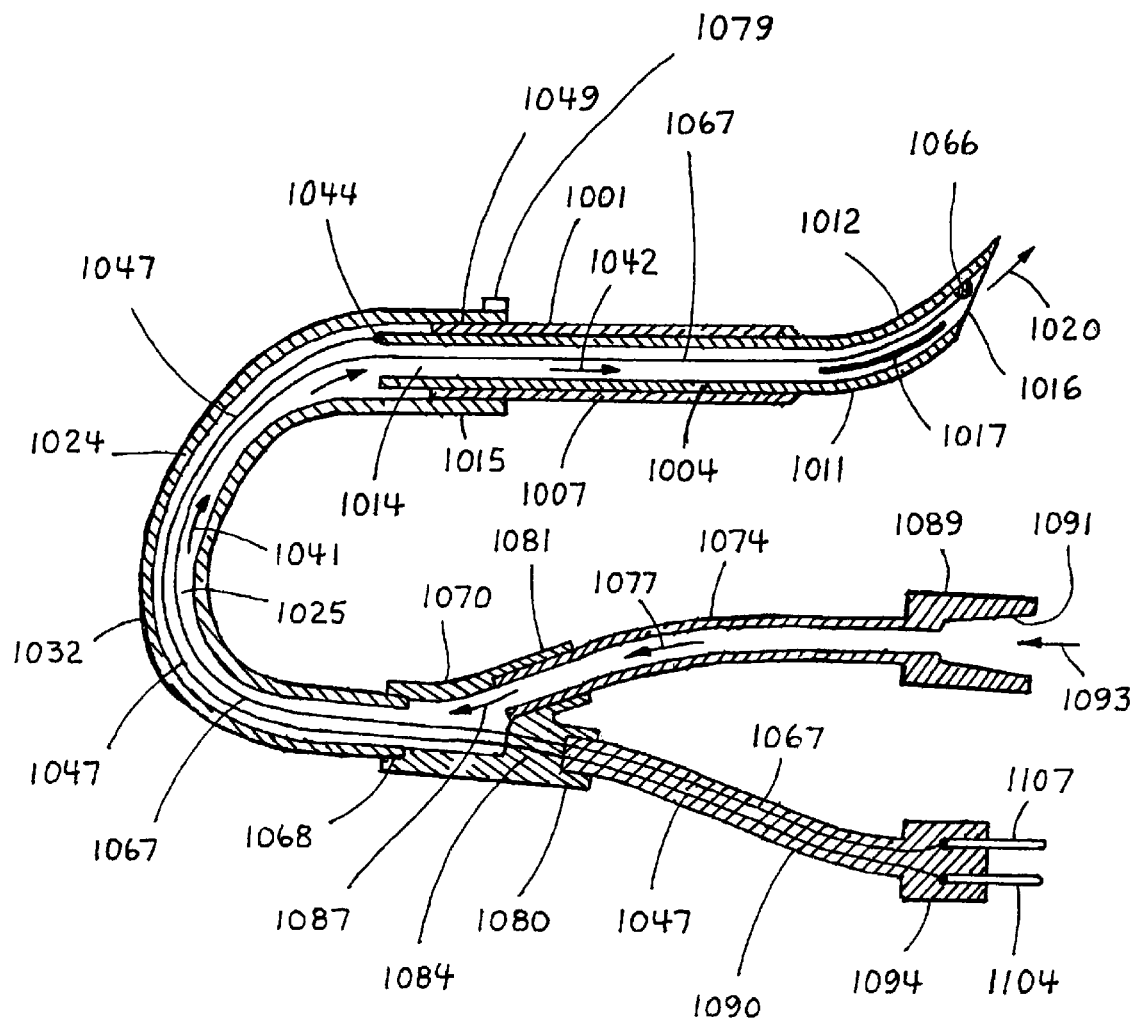
FIG. 21 is a schematic diagram showing a system with an integrated RF electrode including a needle having a unitized flexible injection and TC/RF connections.

Referring to FIG. 21, a unitized RF, TC, and injection high frequency electrode system is shown schematically in sectional view. The electrode 1001 can include a cannula that, in one example, can be a metal tubing 1004 that is insulated over at least a portion of its surface by insulation 1007. The metal tubing 1004 can have an uninsulated electrode tip 1011 at its distal end. In one example, tip 1011 can have a curved shape such as 1012, and it can have a sharpened beveled distal tip 1016. In another example, the distal end of the electrode 1001 can have a straight tip shape, and the pointed structure of the tip can be of a different form, as illustrated in the other figures and embodiments described herein. In one example, there can be a radio opaque element, such as the heavy metal wire segment 1017, inside the lumen of uninsulated electrode tip so that the position, the uninsulated length, and the direction of the curved tip direction can be visualized under x-ray imaging of the electrode after it has been inserted into the patient's body. For example, the radio opaque element 1017 can be tungsten, tantalum, platinum, silver, gold, or other heavy atomic number metal or material segment. Element 1017 can be bonded, glued, or welded to the interior of the metal tubing 1004 as long as it does not obstruct the flow of the injected fluid through the metal tubing 1004. The length of the radio opaque element 1017 can be about the same length as the uninsulated electrode tip portion of the electrode 1001 such that the length of the radio opaque element as seen on an x-ray indicates the length of the uninsulated electrode tip. In another aspect, the radio opaque element can be curved or can follow the curved direction of the bent tip portion 1012, so that under x-ray imaging the clinician can see the direction that the curve is pointing in the target tissue. A temperature sensor 1066 can be in thermal contact with the wall of the metal tubing 1004. For example, 1066 can be a TC sensor that includes a welded junction of a TC wire 1067 to the inner wall of the metal tubing at position 1066. In another example, element 1067 can comprise two wires such as copper and constantan that can be electrically joined at 1066 and positioned in thermal contact with the wall of the metal tubing. The distal end of flexible tubing 1024 can be joined to the proximal end of the metal tubing and fluid sealed, as for example, at the joint 1049. In one example, the flexible tubing can be made of flexible plastic such as polyurethane, PVC, polyethylene or other materials, and can be bonded to the metal tubing by various glues. In another example, the distal end of the plastic tubing 1024 can be slipped over the proximal end of the metal tubing and/or the proximal end of the insulation portion of the metal tubing and bonded at that position to form a fluid seal. In another example, a hub (not shown) can be bonded to the proximal end of the metal tubing and also bonded to the tubing 1024 to mechanically attach and fluid seal the elements together. Examples of proximal end hub structure are illustrated in for example, FIG. 22. The tubing 1032 at the proximal end of the metal tubing, or, if a hub is used, the hub at the proximal end of the metal tubing can have, in one example, a tab or a marker as illustrated by the marker 1079, located at end 1015, to show in which direction the curved portion of the tip 1012 is pointing. One advantage of this marker 1079 is that when the electrode is inserted into the patient's body, the clinician, by looking at the marker 1079 on the proximal end on the metal tubing shaft can determine the direction of the curve of the needle tip and thus better assess how to navigate the electrode properly to the target tissue. For example, the marker can be a tab, a painted marking, or other visual or tactile marker. The flexible tubing can have an inner lumen 1025 that can carry RF and TC wires such as 1047 and 1067, respectively, and can be also the conduit for injected fluid that can flow inside the inner lumen as represented by the arrow 1041. In another example, the single flexible leader tubing section 1024 can have more than one inner lumen 1025, for example, a first lumen containing the RF and the TC wires 1047 and 1067, and a second lumen containing the injected fluid flow as illustrated by arrow 1041. In another example, the single flexible tubing 1024 can comprise one inner lumen that carries the fluid flow, and the high frequency wires and the TC wires can be molded directly into the wall of the single flexible tubing 1024. One advantage of the single unitized flexible leader such as tubing 1032 in FIG. 21 is that it reduces the complexity of the tubing structures that are attached to the shaft of 1001. Another advantage is that a single leader reduces the encumbrances of the electrode system near the patient and thus keeps the surgical area around the insertion site of the electrode 1001 uncluttered. Another advantage is that the single leader reduces the drag and weight of the connections to the electrode which reduces the chances that the electrode will be moved form its desired target position.

Referring to FIG. 21, the single flexible leader 1024 connects to a junction element 1070 by a fluid tight junction 1068. Junction element 1070 can be for example, y-shaped with continuing arms or elements 1080 and 1081 that connect to flexible tubings 1090 and 1074, respectively, through region 1084. Tubing 1090 carries the RF and TC wires 1047 and 1067, respectively, on to the connector 1094 and connect electrically to contacts or pins 1104 and 1107, respectively. The interior of tubing 1090 can be fluid sealed or blocked from the injection fluid so that the fluid will not enter the connector 1094. In one example, another flexible tubing 1074 can be joined to the junction element 1070 at the element 1081 by a fluid seal. Tubing 1074 can carry the injected fluid as indicated by the arrow 1077. Tubing 1074 can be connected to the injection hub 1089, which in one example, can have a luer or other fluid connection port 1091 to enable coupling to a fluid source. The fluid source can provide injection of fluid into the port hub 1089 as indicated by the arrow 1093. Fluid injected into the port 1089 can flow through tubing 1074, such as arrow 1077, through electrode junction 1070, such as arrow 1087, through the unitized fluid/RF/TC flexible leader 1032, such as arrow 1041, through the inner space 1014 of the needle portion, such as arrow 1042, and out of the distal end of the cannula structure, such as arrow 1020. The electrical connections 1104 and 1107 can connect for example, to a connection cable (not shown) that connects to a high frequency generator (not shown) which supplies signal outputs and which can read out the temperature from the TC sensor such as 1066. The connection 1104 can be connected to the RF wire or wires 1047 that can be, in one example, electrically connected to the metal tubing 1004 at the junction 1044.

Referring to FIG. 21, in one aspect, the single flexible leader 1032 can provide a simple, unobtrusive, and convenient conduit of the high frequency, TC and injected fluid between the cannula portion of the electrode that is inserted into the patient's body and the sources of signal output, TC readout, and fluid input. One advantage is that there are not two separate leaders, one for the high frequency and TC connections and another for the fluid injection connections, attached directly to the proximal end or to the hub of the metal tubing shaft of the electrode. This has the advantage of simplifying the connections to the electrode at the site of the electrode insertion. Another advantage is that there is less clutter of tubing and wires near the electrode at the patient's insertion site, which can be confusing and distracting to the clinician. Another advantage is that there are less tubes and wires to get entangled near the patient, and this can be especially the case when multiple electrodes are inserted into the patient's body in close proximity, as is often done, for multiple level high frequency treatment in the spinal region. Another advantage is that there is one unified tubing connected to the proximal end of the electrode shaft which will have less drag that the case of that there are two separate connections to the proximal end of the electrode cannula one for the fluid injection and one for the high frequency/TC connections.

Referring to FIG. 21, the length of the single unitized flexible leader portion 1032, that contains in one compact tubing, the high frequency wires 1047, the TC wires 1067, and the fluid channel is the length of the leader structure between the connection of the flexible leader 1032 to the proximal end of the shaft of electrode 1001 and the junction element 1070. This unitized leader length can be made to suit clinical needs, sterility requirements, desire to minimize drag on and movement of the electrode from manipulations, and convenience in the surgical setting. In one example, the unitized leader length can be in the range of about 0.2 to 5 centimeters, or about 0.1 to 2 inches, or less, if the requirements or problems to reduce the drag or weight of connections on the electrode are not very severe. In another example, the unitized leader length can be made in the range of about 5 to 30 centimeters, or about 2 to 12 inches, if there is a need to remove the junction element 1070 to a more distant position from the surgical field. For example, this may be required for reasons of criticality of the sterile field so that the electrical connections and the fluid connection must kept far for the electrode insertion sight. In another example, if, due to the presence of multiple electrode placements in close proximity, the field around the electrodes must be keep as clear as possible, then unitized leader length lengths of about 5 to 30 centimeters, or about 2 to 12 inches, or longer can be important. In another example, if there is a need too reduce the drag on the electrode the has been placed in the patient's body, then it can be important to remove the point of connection of the fluid port and the high frequency/TC connection to the high frequency generator to sufficient desired distance from the electrode insertion sight, and this can require the unitized leader length to be in the range: about 10 to 30 centimeters (about 4 to 12 inches); or about 30 to 50 centimeters (about 12 to 20 inches); or about 50 to 100 centimeters (about 20 to 40 inches); or about 100 to 1000 centimeters (about 40 to 400 inches); or more, depending on the clinical procedure and operating environment. In one example, the unitized leader length may be needed to bring the high frequency generator and fluid connection well away from the surgical or sterile field as in the case that the high frequency generator must be in another room as for example, in the setting of an MRI scanner procedure room, or if it must be clear of anesthetic and other support equipment.

Figure 22:
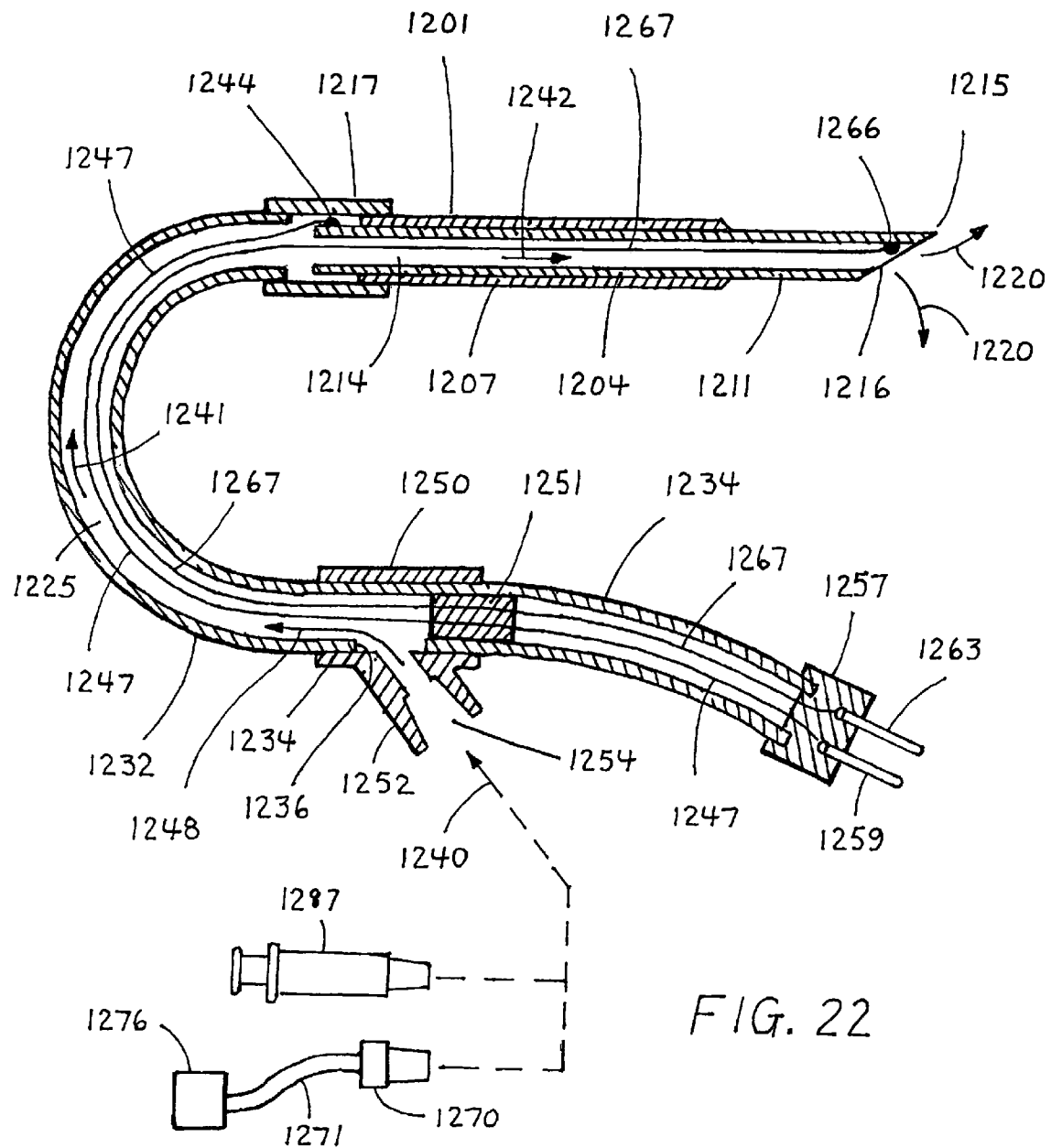
FIG. 22 is a schematic diagram showing a system with an integrated RF electrode including a needle having a unitized flexible injection and TC/RF connections.

Referring to FIG. 22, an integral injectable electrode 1201 is shown in schematic and sectional view. Rigid metal tubing 1204 is insulated over part of its length by insulation 1207. There is an uninsulated electrode tip portion 1211. In one example, the uninsulated electrode tip 1211 can have a straight shape and can have a bevel shaped point 1216 and a sharp tissue piercing tip point 1215. TC wires 1267 can pass inside the metal tubing 1204 in its inner space 1214, and can connect at the distal end to a TC junction 1266 which is in thermal contact with the wall of the metal tubing 1204. The TC wire(s) 1267 can run back through the proximal end of metal tubing 1207 and into the flexible leader tubing 1232. Also inside flexible leader tubing 1232 is the high frequency wire or wires 1247 that carries high frequency signal output from a high frequency generator (not shown) to the electrical junction 1244 with the metal tubing 1204. The inner space or the inner lumen 1225 of the single flexible tubing 1232 can carry the fluid that is flowing as indicated by the arrow 1241. The flexible leader tubing 1232 can be joined by a fluid sealed joint to a junction element 1250 at 1234. This junction element 1250 can be at a sufficient distance away from the proximal end or the proximal hub 1217 to suit ergonomic and clinician needs. Distance ranges as described in connection with the flexible tubing in FIG. 21 can apply to the single flexible leader length 1232. Junction element 1250 can have a fluid port element 1252 that has an injection port portion 1254, which in one example, can be a luer taper or, in another example, a slip or other type of adaptor to enable coupling of a fluid source to the junction element. In one example, a syringe 1287 can be coupled to the port 1254 (illustrated by the dashed lines) to inject fluid into the junction 1250 as shown by the arrow 1240. In another example, a fitting 1270 couples to port 1254, and connects by a flexible fluid line 1271 to a fluid source 1276. Source 1276 can in one example, be an automatic fluid pump or infusion apparatus that can infuse, for example, saline into the electrode system to the target tissue to provide a continuous low impedance pathway for more effective high frequency current and/or high frequency voltage applied to the target tissue. The continuation leader tubing 1234 that carries the high frequency wires 1247 and the TC wires 1267 to the electrical connection 1257 which connects the wires 1247 and 1267 to the contacts and/or pins 1259 and 1263, respectively can be joined to the junction element 1250 The connection 1257 can be connected further to an intermediate connection cable and on to a high frequency generator, or can be connected directly to a high frequency generator. The high frequency generator can supply signal output to the uninsulated electrode tip 1211 through the connection wire 1247 and the metal tubing 1204. The high frequency generator can also readout the temperature at the TC 1266 by the signal through the TC wire(s) 1267.

Referring to FIG. 22, the single flexible tubing structure of tubing 1232 can carry all together in its inner lumen 1225 the high frequency wires 1247, TC wires 1267, and the injected fluid. Fluid injected into port 1254, as illustrated by arrow 1240, can flow through the tubing 1232, as illustrated by arrows 1248 and 1241, pass through the metal tubing interior, as illustrated by arrow 1242, and exit from the distal end of the tip 1211, as illustrated by arrow 1220, into the target tissue when the electrode 1201 is inserted into the living body. The junction 1250 can be at a distance from the proximal end or hub 1217 of the electrode 1201 according to clinical requirements. In one example, the element 1250 can be in the range of 5 to 100 centimeters away from hub 1217. In another example, the element 1252 can be in the range of 100 to 500 centimeters or more if a very remote direct connection to the fluid source and the high frequency generator is convenient for the clinician or the patient arrangement. The distance ranges as described for the flexible leader length in FIG. 21 can also be applied in connection with FIG. 22. One advantage is that the electrode system 1201 and its leader structures 1232 and 1234 and the port 1254 can be presterilized, and the port 1254 and connection 1257 can then be lying in areas that are farther from the surgical sight and are less sterile than the immediate electrode insertion sight. Such more distant sights are for example, where the clinician manipulates the port 1254 to connect a fluid source such as 1267 and where the clinician can manipulate connection 1257 to connect up the high frequency generator. It is an advantage to perform fewer manipulations at a distance from the cannula itself to avoid the risk of contamination of the surgical site. Another advantage is that the single leader structures 1232 and 1234 make the surgical site less encumbered and simple. For example, if several electrodes are being inserted into the patient's back at the same treatment, the reduced presence of wire and tubing reduces the complexities which can result in less chance of errors and confusion.

Referring to FIG. 22, the flexible tubing 1232 and the tubing 1234 can, in one example, be a continuation of the same flexible tubing. For example, 1232 and 1234 can be a single rubber or plastic tubing. In one example, a hole 1236 can be cut in the tubing 1234, and the junction element 1250 can be slipped over the tubing in assembly and bonded to the tubing by glue or solvent. A plug 1251 can be placed in the tubing extension portion 1234 so that fluid injected into port 1254 will not reflux back into the tubing 1234 and potentially electrically short out the connections at the contacts 1259 and 1263. Another advantage is that the single leader structure as illustrated in FIG. 22 reduces the weight and the drag on the electrode once it is positioned in the patient's body. The single leader construction can be made very lightweight and unobtrusive. For example, the flexible tubing 1232 can be made of very flexible plastic tubing in the outer diameter range of 1 to 3 millimeters, or less, and the high frequency and the TC wires inside the inner lumen of the tubing can be in the range of diameter of 0.1 to 0.3 millimeters or less. In another example, the wires can be larger for example, in the range of 0.3 to 0.6 millimeters, if larger inner diameter and outer diameter flexible plastic tubing is used, depending of the clinical context anticipated. The high frequency and the TC wires 1247 and 1267 can be insulated over the lengths that are inside the fluid carrying portions of the leaders 1223 and 1234, so that for example, if ionic fluid such as saline are injected into the leader tubing, there will not be electrical currents flowing between the wires as this may cause errors, for example, in the temperature readings from the TC sensor 1266.

Figure 23:
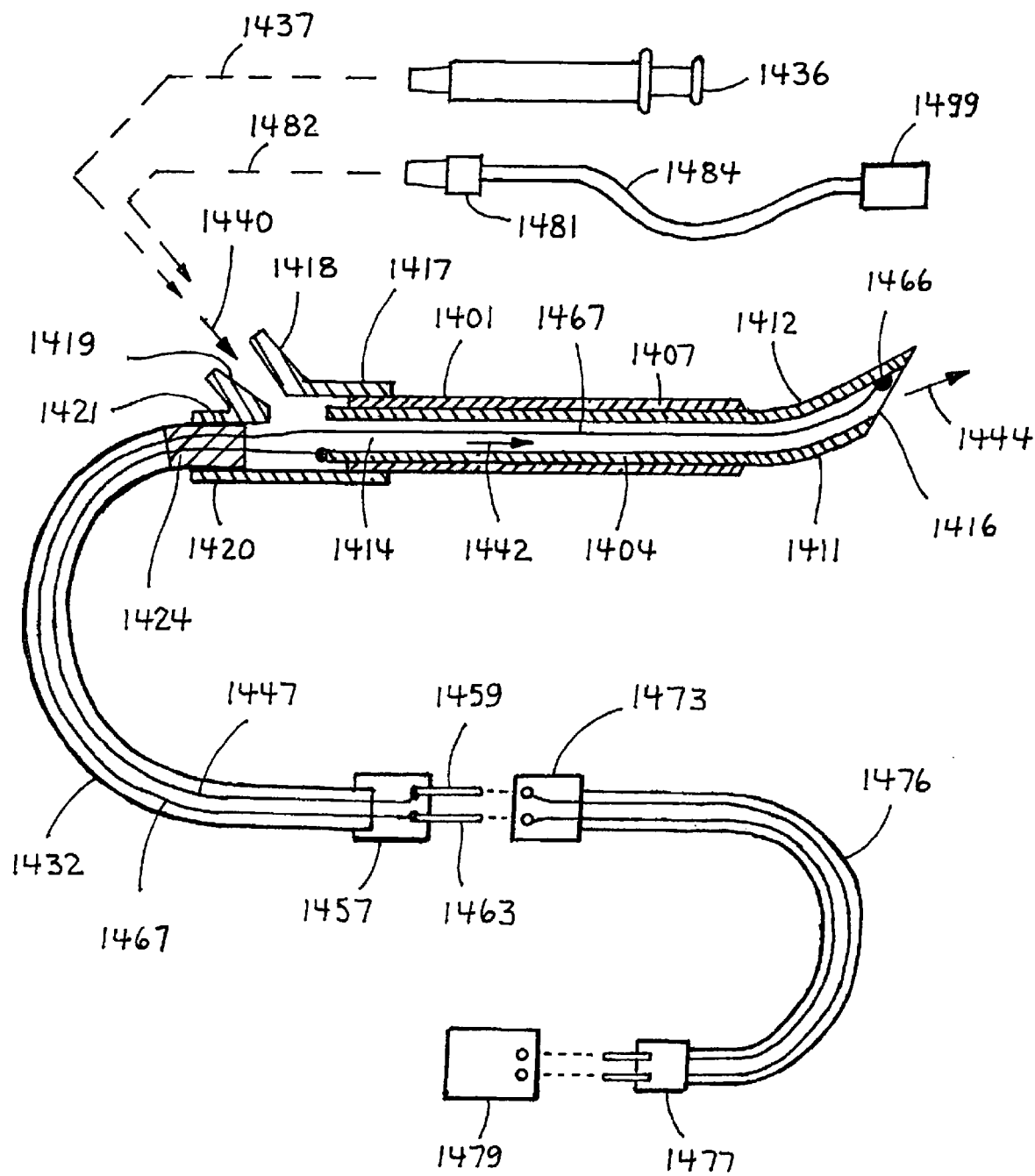
FIG. 23 is a schematic diagram showing a system with an integrated RF electrode including a needle having a flexible TC/RF leader connections and an inflexible injection port.

Referring to FIG. 23, a unitized high frequency injectable electrode 1401 is illustrated in schematic and in sectional view. The electrode 1401 can include a rigid metal tubing 1404 that is insulated over a portion of its length by insulation 1407. The proximal end can have an uninsulated electrode tip 1411 that has a curved or bent shaped portion 1412, and the point can include a bevel 1416. TC wire(s) can run on the inside of the metal tubing. A hub element 1417 can be attached, for example, bonded to the proximal end of the metal tubing 1404 and can have a rigid or non-flexible fluid injection port 1418 that includes a hub port 1419 to enable coupling of the hub 1417 to a fluid source. In one example, the hub port 1419 can be a luer type coupling, or in another example, the fitting 1419 can be a fluid coupling such as a slip fitting or a locking fitting. In one example, the injection port 1418 can be extended out from the hub 1417 in an azimuthal direction that indicates the direction the curved distal end tip 1412 as shown in FIG. 23. One advantage of this is that when the electrode 1401 is inserted into the patient's body, the clinician can see from the orientation, or the azimuthal angle of the injection port 1418 with respect to the direction of the shaft of electrode 1401. This enables the clinician to determine which direction the curved tip 1412 must be pointing inside the tissue of the patient's body. This can help the clinician guide and steer the bent uninsulated electrode tip 1412 to a desired position with respect to the target tissue. Also, the hub 1417 has a high frequency and a TC attachment portion 1420 to which is attached a flexible leader element 1432 at the joint 1421. The flexible leader for example, can include a flexible plastic tubing that carries the high frequency wires 1447 and the TC wire(s) 1467. In one example, the single flexible tubing 1432 can have at least one tubing lumen through which the wires 1447 and 1467 pass. In another example, the flexible leader tubing 1432 can have no inner lumen, and it can be, for example, a plastic element with the wires 1447 and 1467 molded or embedded inside it. The flexible leader tubing 1432 can connect to a connection hub 1457 that includes contacts 1459 and 1463 that electrically connect to the wires 1447 and 1467, respectively. The connection 1457 can connect to a connection cable 1476 at cable hub 1473, and cable 1476 can make connection at its other end hub 1477 to a high frequency generator 1479 to enable supplying signal output to the electrode 1401 and TC readout of the temperature at the TC sensor 1466. In one example, a plug or fluid sealed portion 1424 inside the leader tubing 1432 prevents fluid which is injected into the port 1418, from flowing through the leader 1432 and into the connection 1457 and causing electrically faulty or shorted conditions at 1457. Various forms of fluid sources can be used to inject fluid into the hub port 1418. In one example, a syringe 1436 can be connected to the port connection 1419, as illustrated by the dashed line 1437. In another example, a fluid coupler 1481 can be connected to the fluid port 1418 as illustrated by the dashed line 1482. Coupler 1481 connects to flexible tubing 1484 that connects to fluid source 1499. Fluid from a fluid source injected into port element 1418 can flow into the port, as illustrated by the arrow 1440, through the lumen 1414 of the metal tubing 1404, as illustrated by the arrow 1442, and out of the proximal end of the electrode, as illustrated by the arrow 1444.

The electrode system and the methods described herein can be used to treat many target tissue in a patient's body other than just spinal nerves. For example, the system and methods can be used to treat neural structures in the inter-vertebral disc. In one example, the electrode system configurations shown in the FIGS. 1-20 can be used for inserting the electrode tip into the inter-vertebral disc and applying high frequency signal output to the disc material and neural structures or the treatment of pain or for the alteration of the disc material in order to change it for clinical purposes such as for sealing disc tears or for shrinking or denaturating the disc material. In one example, the high frequency signal can be a RF signal, either a continuous wave or a pulsed type sequence. In another example, the system and method can be used to treat the dorsal root ganglion. For example, the dorsal root ganglion can be in the cervical region to treat neck pain or other disorders. In another example, the dorsal root ganglion can be in the thoracic or the lumbar region to treat various neurological disorders or pain problems, including back pain, post surgical pan, reflex sympathetic dystrophy, and spasticity. In another example, the electrode system and methods shown in the FIGS. 1-20 can be used in the brain or the spinal cord to treat movement disorders, pain disorders, epilepsy, or other diseases. In one aspect, the electrode system and method of FIGS. 1-20 can be used to treat neuro-musculature disorders. The electrode system can be inserted into the superficial tissues of the back, legs, hands, feet, scalp and other target tissues to treat pain, weakness, spasticity, or other disorders. Continuous or pulsed RF signals can be used in all examples herein, depending on the clinical needs.

A number of embodiments of the invention have been described. Nevertheless, it will be understood that various modifications may be made without departing from the spirit and scope of the invention. Accordingly, other embodiments are within the scope of the following claims.

What is claimed is:

1. A unitized high frequency electrode system comprising:
a cannula having a proximal end and a distal end, the distal end comprising an uninsulated electrode tip, and the cannula being rigidly adapted to enable self-supported penetration of skin and tissue so that the uninsulated electrode tip can be positioned in a target tissue;
a unitized flexible leader having an inner lumen, the unitized flexible leader being inseparably connected to the proximal end of the cannula;
a high frequency electrical connection carried, at least in part, in the unitized flexible leader to the proximal end of the cannula where the high frequency electrical connection is inseparably connected to the proximal end of the cannula and configured so that a high frequency signal connected to the high frequency electrical connection is connected to the uninsulated electrode tip;
a temperature connection and a temperature sensor, the temperature sensor configured to be in thermal contact with the uninsulated electrode tip, the temperature connection being carried, at least in part, in the unitized flexible leader to the proximal end of the cannula and being connected to the temperature sensor; wherein the temperature connection is configured so that a temperature readout apparatus connected to the temperature connection can read the temperature at the temperature sensor;

whereby, the high frequency electrode system, when inserted into the living body so that the uninsulated electrode tip is positioned in the tissue, enables the treatment of the tissue by applying the high frequency signal to the tissue while sensing the temperature of the tissue adjacent to the uninsulated electrode tip.

2. The system of claim 1, wherein the high frequency electrical connection includes a flexible high frequency portion.

3. The system of claim 1, wherein the temperature connection includes a flexible temperature portion that is inseparably connected to the proximal end of the cannula.

4. The system of claim 1, wherein the tissue is near a spinal nerve.

5. The system of claim 1, wherein the tissue is near spinal bones.

6. The system of claim 1, wherein the uninsulated electrode tip comprises a metal tubing at its exterior surface.

7. The system of claim 6, wherein the temperature sensor is in thermal contact with the metal tubing to enable rapid temperature measurement of the target tissue adjacent to the uninsulated electrode tip.

8. The system of claim 6, wherein the metal tubing includes a diameter of at least 0.4 millimeters.

9. The system of claim 1, wherein the flexible leader includes an injection port, and the cannula further comprises a fluid channel through the cannula and a fluid exit at the distal end of the cannula, whereby fluid can be injected into the injection port and pass through the fluid channel and out of the cannula through the fluid exit.

10. The system of claim 9, wherein the injection port further comprises a flexible fluid port connection.

11. The system of claim 1, wherein the flexible leader portion comprises a distal leader end and a proximal leader end, the distal leader end being connected to the proximal end of the cannula and the proximal leader end being connected to a unitized hub that is adapted to connect to a high frequency generator.

12. The system of claim 11, wherein the flexible leader portion comprises a single flexible tubing, the high frequency electrical connection comprises at least one high frequency electrical wire, the temperature connection comprising at least one temperature wire, and the cannula further comprising a fluid channel through the cannula and a fluid exit channel near the distal end of the cannula, the inner lumen being fluidly connected to the fluid channel in the cannula, and wherein the system further comprises an injection port, whereby fluid injected into the injection port passes through the inner lumen, through the fluid channel, and out of the cannula through the fluid exit channel.

13. The system of claim 12, wherein the cannula comprising a metal tubing, and the flexible leader comprises a single flexible plastic tubing, the inner lumen being a single lumen within the single flexible plastic tubing, the distal leader end being connected to the metal tubing, and the proximal leader end being connected to the hub connection and the injection port.

14. The system of claim 1, wherein the temperature connection comprises a wire that runs in part through the interior space of the cannula and connects to the temperature sensor.

15. The system of claim 1, wherein the proximal end is configured to be inaccessible to port-injection of fluid.

16. The system of claim 1, wherein the proximal end is closed to injection of fluids into the interior space of the cannula.

17. The system of claim 1, wherein the proximal end is sealed to the passage of fluids through the interior space of the cannula.

18. The system of claim 1, wherein the distal end of the cannula includes a curved portion to improve the positioning of the uninsulated electrode tip near the target tissue.

19. The system of claim 1, wherein the cannula comprises a metal tubing.

20. The system of claim 1, wherein the uninsulated electrode tip includes a sharpened tip end.

21. The system of claim 20, wherein the sharpened tip end comprises a tri-cut beveled point.

22. The system of claim 1, wherein the temperature sensor comprises a constantan wire that passes through the an interior space of the cannula and is fused electrically to the wall of the metal tubing at the uninsulated electrode tip.

23. The system of claim 1, wherein the temperature sensor comprises a copper and a constantan wire electrically fused to a thermocouple junction.

24. The system of claim 1, wherein the system further includes a radio opaque material inside a lumen of the cannula near the uninsulated electrode tip to increase the contrast in an x-ray imaging of the electrode.

25. The system of claim 19, wherein a lumen at a beveled portion of the metal tubing at the distal end of the cannula is occluded.

26. The system of claim 25, wherein the lumen is occluded by an epoxy.

27. The system of claim 19, wherein the distal end includes a sharpened distal tip that is not fully enclosed by metal.

28. The system of claim 27, wherein the sharpened distal tip comprises a beveled portion of the metal tubing.

29. The system of claim 19, wherein a distal end of the metal tubing comprises a tapered forming of the metal tubing that converges to a tissue piercing tip end.

30. The system of claim 19, wherein the cannula is adapted so that fluid can be injected into the proximal end, through the cannula, and out of the distal end.

31. The system of claim 19, wherein the uninsulated electrode tip comprises at least a portion of the distal end of the metal tubing.

32. The system of claim 20, wherein the sharpened tip end comprises a bevel.

33. The system of claim 19, wherein the uninsulated electrode tip includes a sharpened tip end comprising a beveled portion of the metal tubing.

34. The system of claim 19, wherein the uninsulated electrode tip includes a sharpened tip end comprising at least in part a shaped portion of the distal end of the metal tubing.

35. The system of claim 34, wherein the shaped portion of the distal end of the metal tubing comprises a tapered form of the metal tubing that converges to a tissue piercing tip end.

36. The system of claim 1, further comprising a flexible fluid carrying portion within the cannula.

37. The system of claim 1, wherein the unitized flexible leader comprising a single flexible tubing having at least one lumen channel within the single flexible tubing, the unitized flexible leader having a leader proximal end and a leader distal end, the leader distal end being connected to the proximal end of the cannula so that the at least one lumen channel is connected to the proximal end of the cannula and an injection port that is connected to the leader proximal end and configured so that a fluid injected into the injection port passes through at least one lumen channel, through a proximal opening at the proximal end of the cannula, through a cannula lumen, and out of the cannula lumen through a distal opening at the distal end of the cannula; and wherein the cannula lumen within the cannula connects the proximal opening to the distal opening.

38. The system of claim 37, wherein the leader distal end is inseparably connected to the proximal end of the cannula.

39. The system of claim 37, wherein the electrical connection is connected to the leader proximal end and is adapted to connect to a high frequency generator.

40. The system of claim 37, wherein the single flexible tubing further comprises a plastic tubing having an inner lumen configured so that fluid injected into the injection port passes through the inner lumen and through the cannula lumen to exit the cannula through the distal opening.

41. The system of claim 40, wherein the temperature connection and the high frequency electrical connection comprise wires that pass within the inner lumen of the plastic tubing.

42. The system of claim 40, wherein the high frequency electrical connection and the temperature connection further comprises wires that are at least in part imbedded into the wall of the single flexible tubing.

43. The system of claim 37, wherein the single flexible tubing further comprises a plastic tubing having a first inner lumen configured so that the fluid injected into the injection port passes through the inner lumen and through the cannula lumen to exit the cannula through the distal opening, and a second inner lumen which contains wires that are a part of the high frequency electrical connection and the temperature connection.

44. The system of claim 37, wherein the single flexible tubing between the leader distal end and the position of the injection port on the single flexible tubing has a length in the range of about 0.2 to 2 inches.

45. The system of claim 37, wherein the single flexible tubing between the leader distal end and the position of the injection port on the single flexible tubing has a length in the range of about 2 to 12 inches.

46. The system of claim 37, wherein the single flexible tubing between the leader distal end and the position of the injection port on the single flexible tubing has a length in the range of about 12 to 20 inches.

47. The system of claim 37, wherein the single flexible tubing between the leader distal end and the position of the injection port on the single flexible tubing has a length in the range of about 20 to 40 inches.

48. The system of claim 37, wherein the single flexible tubing between the leader distal end and the position of the injection port on the single flexible tubing has a length in the range of about 40 to 400 inches.

49. The system of claim 37, wherein the cannula further comprises a metal tubing, and wherein the single flexible plastic tubing has a single lumen, the leader distal end being connected to the metal tubing, and the leader proximal end being connected to an electrical hub connection that connects the high frequency electrical connections and the temperature connection to a high frequency generator, and the leader proximal end connects the tubing lumen to the injection port.

50. The system of claim 37, wherein the leader proximal end connects to a junction element that comprises a fluid connection to the injection port and an electrical connection that connects the high frequency electrical connection and the temperature connection to a high frequency generator.

51. The system of claim 50, wherein the junction element further comprises having a branch junction with a fluid branch that connects to the injection port and an electrical branch that connects to the high frequency electrical connection and the temperature connection.

52. The system of claim 50, wherein the injection port further comprises a luer fitting.

53. The system of claim 50, wherein the injection port further comprises a fluid coupling fitting.

54. The system of claim 1, further comprising a single flexible leader having a leader proximal end and a leader distal end, the leader distal end being connected to the proximal end and an non-flexible injection port that is rigidly connected to the proximal end and configured so that fluid injected into the injection port passes through the proximal opening, through the cannula lumen, and out of the cannula lumen through the distal opening.

55. The system of claim 54, further comprising a hub that is rigidly connected to the proximal end of the cannula, the hub having a rigidly connected injection port, and the single flexible leader is connected to the hub.

56. The system of claim 54, wherein the single flexible leader comprises an electrical hub connection at the leader proximal end, the electrical hub connection configured to connect the high frequency electrically connection and the temperature connection to a high frequency generator.

57. The system of claim 54, wherein the single flexible leader from the position of the connection between the leader distal end and the proximal end and the position of the electrically leader hub has a length in the range of about 0.2 to 2 inches.

58. The system of claim 54, wherein the single flexible leader from the position of the connection between the leader distal end and the proximal end and the position of the electrically leader hub has a length in the range of about 2 to 12 inches.

59. The system of claim 54, wherein the single flexible leader from the position of the connection between the leader distal end and the proximal end and the position of the electrically leader hub has a length in the range of about 12 to 20 inches.

60. The system of claim 54, wherein the single flexible leader from the position of the connection between the leader distal end and the proximal end and the position of the electrically leader hub has a length in the range of about 20 to 40 inches.

61. The system of claim 54, wherein the single flexible leader from the position of the connection between the leader distal end and the proximal end and the position of the electrically leader hub has a length in the range of about 40 to 400 inches.

62. An injectable high frequency electrode system comprising:
   a cannula comprising a metal tubing, configured to be inserted into a patient's body and having a proximal end, a distal end, a cannula channel and an exit out of the cannula channel on the distal end of the cannula, wherein the distal end comprising an uninsulated electrode tip;
   a fluid port connection inseparably connected to the proximal end configured so that fluid injected into the fluid port will pass through the cannula and exit out of the cannula near the distal end;
   a high frequency electrical connection located at least in part at the proximal end and configured so that a high frequency signal applied to the high frequency electrical connection will be connected to the uninsulated electrode tip; and
   a temperature connection and a temperature sensor, the temperature sensor configured to be built into the uninsulated electrode tip to sense the temperature at the uninsulated electrode tip;

wherein the fluid port connection comprises a flexible fluid carrying portion containing at least one single channel lumen, the single channel lumen being fluidly connected to the cannula and the fluid port connection so that fluid injected into the fluid port connection will pass through the single channel lumen and through the cannula to exit out of the cannula near the distal end, the single channel lumen housing at least a portion of the high frequency electrical connection.

63. The system of claim 62, wherein the uninsulated electrode tip comprises at least a portion of the distal end of the metal tubing.

64. The system of claim 62, wherein the system further comprises a flexible portion that is inseparably connected to the proximal end of the cannula that includes the high frequency electrical connection and the temperature connection.

65. The system of claim 62, wherein the temperature connection comprises a wire that runs in part through an interior space of the cannula and connects to the temperature sensor.

66. The system of claim 62, wherein the uninsulated electrode tip includes a sharpened tip end.

67. The system of claim 66, wherein the sharpened tip end comprises a bevel.

68. The system of claim 66, wherein the sharpened tip end comprises a beveled portion of the metal tubing.

69. The system of claim 66, wherein the sharpened tip end comprises at least in part a shaped portion of the distal end of the metal tubing.

70. The system of claim 69, wherein the shaped portion of the distal end of the metal tubing comprises a tapered forming of the metal tubing that converges to a tissue piercing tip end.

71. The system of claim 62, wherein the uninsulated electrode tip comprises a metal tubing at its exterior surface, and the temperature sensor is in thermal contact with the metal tubing to enable rapid temperature measurement of a target tissue adjacent to the uninsulated electrode tip.

72. The system of claim 71, wherein the metal tubing includes a diameter of at least 0.4 millimeters.

73. The system of claim 62, wherein the system includes an inseparable injection port connected to the proximal end of the cannula, whereby fluid can be injected into the injection port and pass through the cannula channel and out of the exit of the cannula channel.

74. The system of claim 73, wherein the injection port comprises a flexible fluid carrying portion.

75. The system of claim 74, wherein the flexible fluid carrying portion comprises a flexible tubing portion containing at least one single channel lumen, the single channel lumen being fluidly connected to the cannula channel and the injection port so that fluid injected into the injection port will pass through the single channel lumen and through the fluid channel to exit from the fluid channel exit, the single channel lumen housing at least a portion of the temperature connection.

76. The system of claim 64, wherein the system further comprises a unitized hub connection at the proximal end that is adapted to connect to a high frequency generator.

77. The system of claim 62, wherein the temperature connection comprises a wire that runs in part through an interior space of the cannula and connects to the temperature sensor.

78. The system of claim 62, wherein the distal end of the cannula includes a curved portion to improve the positioning of the uninsulated electrode tip near a target tissue.

79. The system of claim 62, the single channel lumen further housing at least a portion of the temperature connection.

\* \* \* \* \*